United States Patent
Greenlee et al.

(10) Patent No.: US 7,511,152 B2
(45) Date of Patent: Mar. 31, 2009

(54) ESTROGEN RECEPTOR MODULATORS

(75) Inventors: Mark L. Greenlee, Plainfield, NJ (US); Dongfang Meng, Westfield, NJ (US); Donald M. Sperbeck, East Hanover, NJ (US); Kenneth J. Wildonger, Bridgewater, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/792,729

(22) PCT Filed: Dec. 5, 2005

(86) PCT No.: PCT/US2005/043859

§ 371 (c)(1), (2), (4) Date: Jun. 7, 2007

(87) PCT Pub. No.: WO2006/062876

PCT Pub. Date: Jun. 15, 2006

(65) Prior Publication Data

US 2007/0265318 A1 Nov. 15, 2007

Related U.S. Application Data

(60) Provisional application No. 60/634,785, filed on Dec. 9, 2004.

(51) Int. Cl.
- *C07D 249/16* (2006.01)
- *C07D 403/00* (2006.01)
- *C07D 249/04* (2006.01)
- *A61K 31/41* (2006.01)

(52) U.S. Cl. ............. 548/261; 548/255; 548/257; 548/259; 514/359

(58) Field of Classification Search ............ 548/255, 548/257, 259, 261; 514/359
See application file for complete search history.

(56) References Cited

U.S. PATENT DOCUMENTS

| | | | |
|---|---|---|---|
| 6,380,225 | B1 | 4/2002 | Assmann et al. |
| 7,087,599 | B2 | 8/2006 | Parker, Jr. et al. |
| 7,151,196 | B2 | 12/2006 | Wilkening et al. |

FOREIGN PATENT DOCUMENTS

| | | | | |
|---|---|---|---|---|
| WO | WO 84/02131 | * | 6/1984 | ......... 548/200 |
| WO | WO 01/49288 | * | 7/2001 | ......... 548/200 |
| WO | WO 01/97788 | * | 12/2001 | ......... 548/200 |
| WO | WO 02/41835 |   | 5/2002 | |

OTHER PUBLICATIONS

Golub et al. Science (1999), vol. 286 521-537.*
Lala et al. Cancer and Metastasis Reviews (1998), 17(1), 91-106.*
Gripenberg, M, Scand. J. Rheumatology, vol. 10 (2) 1981, 85-91.*
"Dementia." Retrieved online via Internet [May 14, 2008] URL: www.nlm.nih.gov/medlineplus/dementia.html#cat5.*
"Autism." Retrieved online via Internet [May 14, 2008] URL: www.nlm.nih.gov/medlineplus/autism.html.*
"Attention deficit hyperactivity disorder." Retrieved online via Internet [May 14, 2008] URL: www.nlm.nih.gov/medlineplus/attentiondeficithyperactivitydisorder.html#cat3.*
"Anxiety." Retrieved online via Internet [May 14, 2008] URL: www.nlm.nih.gov/medlineplus/anxiety.html#cat3.*
"Parkinson's Disease." Retrieved online via Internet [May 14, 2008] URL: www.nlm.nih.gov/medlineplus/parkkinsonsdisease.html.*
"Cancer." Retrieved online via Internet [May 14, 2008] URL: www.nlm.nih.gov/medlineplus/cancer.html.*

* cited by examiner

Primary Examiner—Kamal A. Saeed
Assistant Examiner—Samantha L Shterengarts
(74) Attorney, Agent, or Firm—Mollie M. Yang; Yong Zhao; Valerie J. Camara

(57) ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, inflammation, inflammatory bowel disease, irritable bowel syndrome, sexual dysfunction, hypertension, retinal degeneration and cancer, in particular of the breast, uterus and prostate.

17 Claims, No Drawings

ESTROGEN RECEPTOR MODULATORS

CROSS REFERENCE TO RELATED APPLICATIONS

This application is a U.S. National Phase application under 35 U.S.C. § 371 of PCT application Ser. No. PCT/US2005/043859, filed Dec. 5, 2005, which claims priority under 35 U.S.C. § 119(e) from U.S. Provisional Application Ser. No. 60/634,785, filed Dec. 9, 2004.

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

The estrogen receptor has been found to have two forms: ERα and ERβ. Ligands bind differently to these two forms, and each form has a different tissue specificity to binding ligands. Thus, it is possible to have compounds that are selective for ERα or ERβ, and therefore confer a degree of tissue specificity to a particular ligand.

What is needed in the art are compounds that can produce the same positive responses as estrogen replacement therapy without the negative side effects. Also needed are estrogen-like compounds that exert selective effects on different tissues of the body.

The compounds of the instant invention are ligands for estrogen receptors and as such may be useful for treatment or prevention of a variety of conditions related to estrogen functioning including: bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression resulting from an estrogen deficiency, inflammation, inflammatory bowel disease, irritable bowel syndrome, sexual dysfunction, hypertension, retinal degeneration and cancer, in particular of the breast, uterus and prostate.

SUMMARY OF THE INVENTION

The present invention relates to compound and pharmaceutical compositions useful for treating or preventing a variety of conditions related to estrogen functioning. One embodiment of the present invention is illustrated by treating or preventing estrogen related disorders with a compound of the following formula, and the pharmaceutically acceptable salts and stereoisomers thereof:

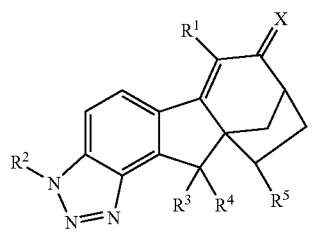

DETAILED DESCRIPTION OF THE INVENTION

The present invention relates to compound and pharmaceutical compositions useful for treating or preventing a variety of conditions related to estrogen functioning. One embodiment of the present invention is illustrated by a compound of the following formula, and the pharmaceutically acceptable salts and stereoisomers thereof:

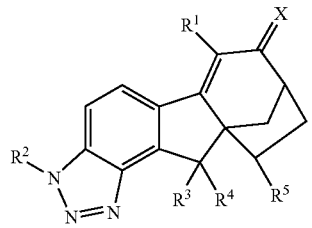

wherein X is O, N—$OR^a$, N—$NR^aR^b$ or $C_{1-6}$ alkylidene, wherein said alkylidene group is optionally substituted with hydroxy, amino, $O(C_{1-4}alkyl)$, $NH(C_{1-4}alkyl)$, or $N(C_{1-4}alkyl)_2$;

$R^1$ is hydrogen, fluoro, chloro, bromo, iodo, $C_{1-4}$alkyl, $C_{2-4}$alkenyl, $C_{2-4}$alkynyl, $C_{3-6}$cycloalkyl, aryl or heteroaryl, wherein said alkyl, alkenyl, alkynyl, cycloalkyl, aryl and heteroaryl groups are optionally substituted with 1, 2 or 3 groups selected from the group consisting of fluoro, chloro, bromo, iodo, cyano and $OR^a$;

$R^2$ is hydrogen, (C=O)$R^a$, (C=O)$OR^a$ or $SO_2R^a$;

$R^3$ is hydrogen, fluoro, chloro, bromo or hydroxy;

$R^4$ is hydrogen, fluoro, chloro, bromo or hydroxy;

or $R^3$ and $R^4$, when taken together with the carbon atom to which they are attached, form a carbonyl group;

$R^5$ is hydrogen, fluoro, chloro or $C_{1-5}$alkyl, wherein said alkyl is optionally substituted with chloro, bromo, iodo, $OR^a$ or 1-5 fluoro;

$R^a$ is selected from the group consisting of hydrogen, $C_{1-4}$alkyl, and phenyl, wherein said alkyl and phenyl groups are optionally substituted with hydroxy, amino, $O(C_{1-4}alkyl)$, $NH(C_{1-4}alkyl)$, $N(C_{1-4}alkyl)_2$, chloro, bromo or 1-5 fluoro, and when two or more $R^a$ are present, they are independently selected;

or a pharmaceutically acceptable salt or stereoisomer thereof.

In a class of the embodiment, X is O or N—$OR^a$. In a subclass of the embodiment, X is O or N—OH. In a further subclass of the embodiment, X is O.

In a class of the embodiment, $R^1$ is hydrogen, fluoro, chloro, bromo, or $C_{1-4}$alkyl, wherein said alkyl group is optionally substituted with 1, 2 or 3 groups selected from the group consisting of fluoro, chloro or bromo.

In a class of the embodiment, $R^2$ is hydrogen.
In a class of the embodiment, $R^3$ is hydrogen.
In a class of the embodiment, $R^4$ is hydrogen.
In a class of the embodiment, $R^5$ is hydrogen.

Non-limiting examples of the present invention include, but are not limited to:

6-(trifluoromethyl)-3,9,10,11-tetrahydro-8,10a-methanocyclohepta[1,2]indeno[4,5-d][1,2,3]triazol-7(8H)-one;
6-chloro-3,9,10,11-tetrahydro-8,10a-methanocyclohepta[1,2]indeno[4,5-d][1,2,3]triazol-7(8H)-one;
6-bromo-3,9,10,11-tetrahydro-8,10a-methanocyclohepta[1,2]indeno[4,5-d][1,2,3]triazol-7(8H)-one;
6-phenyl-3,9,10,11-tetrahydro-8,10a-methanocyclohepta[1,2]indeno[4,5-d][1,2,3]triazol-7(8H)-one;
6-chloro-3,9,10,11-tetrahydro-8,10a-methanocyclohepta[1,2]indeno[4,5-d][1,2,3]triazol-7(8H)-one oxime;
6-(trifluoromethyl)-3,9,10,11-tetrahydro-8,10a-methanocyclohepta[1,2]indeno[4,5-d][1,2,3]triazol-7(8H)-one oxime;
6-phenyl-3,9,10,11-tetrahydro-8,10a-methanocyclohepta[1,2]indeno[4,5-d][1,2,3]triazol-7(8H)-one oxime;
(8R,10aS)-6-(trifluoromethyl)-3,9,10,11-tetrahydro-8,10a-methanocyclohepta[1,2]indeno[4,5-d][1,2,3]triazol-7(8H)-one;
(8R,10aS)-6-chloro-3,9,10,11-tetrahydro-8,10a-methanocyclohepta[1,2]indeno[4,5-d][1,2,3]triazol-7(8H)-one;
(8R,10aS)-6-bromo-3,9,10,11-tetrahydro-8,10a-methanocyclohepta[1,2]indeno[4,5-d][1,2,3]triazol-7(8H)-one;
(8R,10aS)-6-phenyl-3,9,10,11-tetrahydro-8,10a-methanocyclohepta[1,2]indeno[4,5-d][1,2,3]triazol-7(8H)-one;
(8R,10aS)-6-chloro-3,9,10,11-tetrahydro-8,10a-methanocyclohepta[1,2]indeno[4,5-d][1,2,3]triazol-7(8H)-one oxime;
(8R,10aS)-6-(trifluoromethyl)-3,9,10,11-tetrahydro-8,10a-methanocyclohepta[1,2]indeno[4,5-d][1,2,3]triazol-7(8H)-one oxime; (8R,10aS)-6-phenyl-3,9,10,11-tetrahydro-8,10a-methanocyclohepta[1,2]indeno[4,5-d][1,2,3]triazol-7(8H)-one oxime;

and the pharmaceutically acceptable salts and stereoisomers thereof.

Also included within the scope of the present invention is a pharmaceutical composition which is comprised of a compound as described above and a pharmaceutically acceptable carrier. The invention is also contemplated to encompass a pharmaceutical composition which is comprised of a pharmaceutically acceptable carrier and any of the compounds specifically disclosed in the present application. The present invention also relates to methods for making the pharmaceutical compositions of the present invention. The present invention is also related to processes and intermediates useful for making the compounds and pharmaceutical compositions of the present invention. These and other aspects of the invention will be apparent from the teachings contained herein.

Utilities

The compounds of the present invention are selective modulators of estrogen receptors and are therefore useful to treat or prevent a variety of diseases and conditions related to estrogen receptor functioning in mammals, preferably humans.

The compounds of the present invention have advantages over similar compounds known in the art in that they present a more desirable metabolic profile. Drug metabolism can be observed in vitro in human liver microsome assays, see e.g., Regina W. Wang, "Validation of (−)-N-3-benzyl-phenobarbital as a selective inhibitor of CYP2C19 in human liver microsomes," DMD 32:584-586, 2004. Also, the compounds of the present invention have advantages over similar compounds known in the art in that they show a more potent ERβ agonistic effect in vivo as measured by the level of induction of the tryptophan hydroxylase gene (see International Publication WO2004027031 to Merck & Co., Inc.).

A variety of diseases and conditions related to estrogen receptor functioning includes, but is not limited to, bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression resulting from an estrogen deficiency, perimenopausal depression, post-partum depression, premenstrual syndrome, manic depression, anxiety, dementia, obsessive compulsive behavior, attention deficit disorder, sleep disorders, irritability, impulsivity, anger management, multiple sclerosis and Parkinson's disease, inflammation, inflammatory bowel disease, irritable bowel syndrome, sexual dysfunction, hypertension, retinal degeneration and cancer, in particular of the breast, uterus and prostate. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention. The estrogen receptor antagonizing effect can be either an ERα antagonizing effect, an ERβ antagonizing effect or a mixed ERα and ERβ antagonizing effect.

The present invention also relates to methods for eliciting an estrogen receptor agonizing effect in a mammal in need thereof by administering the compounds and pharmaceutical compositions of the present invention. The estrogen receptor agonizing effect can be either an ERα agonizing effect, an ERβ agonizing effect or a mixed ERα and ERβ agonizing effect. A preferred method of the present invention is eliciting an ERβ agonizing effect.

The present invention also relates to methods for treating or preventing disorders related to estrogen functioning, bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression resulting from an estrogen deficiency, inflammation, inflammatory bowel disease, irritable bowel syndrome, sexual dysfunction, hypertension, retinal degeneration and cancer, in particular of the breast, uterus and prostate in a mammal in need thereof by administering the compounds and pharmaceutical compositions of the present invention. Exemplifying the invention is a method of treating or preventing depression. Exemplifying the invention is a method of treating or preventing anxiety. Exemplifying the invention is a method of treating or preventing hot flashes. Exemplifying the invention is a method of treating or preventing cancer. Exemplifying the invention is a method of treating or preventing cardiovascular disease.

An embodiment of the invention is a method for treating or preventing cancer, especially of the breast, uterus or prostate, in a mammal in need thereof by administering the compounds and pharmaceutical compositions of the present invention. The utility of SERMs for the treatment of breast, uterine or prostate cancer is known in the literature, see T. J. Powles, "Breast cancer prevention," Oncologist 2002; 7(1):60-4; Park, W. C. and Jordan, V. C., "Selective estrogen receptor modulators (SERMS) and their roles in breast cancer prevention." Trends Mol Med. 2002 February; 8(2):82-8; Wolff, A. C. et al., "Use of SERMs for the adjuvant therapy of early-stage breast cancer," Ann N Y Acad Sci. 2001 December; 949:80-8; Hou, Y. F. et al., "ERbeta exerts multiple stimulative ffects on human breast carcinoma cells," Oncogene 2004 Jul. 29; 23(34):5799-806; Steiner, M. S. et al., "Selective estrogen receptor modulators for the chemoprevention of prostate cancer," Urology 2001 April; 57(4 Suppl 1):68-72; Lai, J. S. et al., "Metastases of prostate cancer express estrogen receptor beta," Urology 2004 October; 64(4):814-20.

Another embodiment of the invention is a method of treating or preventing metastatic bone disease in a mammal in need thereof by administering to the mammal a therapeutically effective amount of any of the compounds or pharmaceutical compositions described above. The utility of SERMS in the treatment of metastatic bone disease is known in the literature, see, Campisi, C. et al., "Complete resoultion of breast cancer bone metastasis through the use of beta-interferon and tamoxifen," Eur J Gynaecol Oncol 1993; 14(6): 479-83.

Another embodiment of the invention is a method of treating or preventing gynecomastia in a mammal in need thereof by administering to the mammal a therapeutically effective amount of any of the compounds or pharmaceutical compositions described above. The utility of SERMS in the treatment of gynecomastia is known in the literature, see, Ribeiro, G. and Swindell R., "Adjuvant tamoxifen for male breast cancer." Br J Cancer 1992; 65:252-254; Donegan, W., "Cancer of the Male Breast," JGSM Vol. 3, Issue 4, 2000.

Another embodiment of the invention is a method of treating or preventing post-menopausal osteoporosis, glucocorticoid osteoporosis, hypercalcemia of malignancy, bone loss and bone fractures in a mammal in need thereof by administering to the mammal a therapeutically effective amount of any of the compounds or pharmaceutical compositions described above. The utility of SERMs to treat or prevent osteoporosis, hypercalcemia of malignancy, bone loss or bone fractures is known in the literature, see Jordan, V.C. et al., "Selective estrogen receptor modulation and reduction in risk of breast cancer, osteoporosis and coronary heart disease," Natl Cancer Inst 2001 October; 93(19):1449-57; Bjarnason, N H et al., "Six and twelve month changes in bone turnover are realted to reduction in vertebral fracture risk during 3 years of raloxifene treatment in postmenopausal osteoporosis," Osteoporosis Int 2001; 12(11):922-3; Fentiman I. S., "Tamoxifen protects against steroid-induced bone loss," Eur J Cancer 28:684-685 (1992); Rodan, G. A. et al., "Therapeutic Approaches to Bone Diseases," Science Vol 289, 1 Sep. 2000.

Another embodiment of the invention is a method of treating of preventing periodontal disease or tooth loss in a mammal in need thereof by administering to the mammal a therapeutically effective amount of any of the compounds or pharmaceutical compositions described above. The use of SERMs to treat periodontal disease or tooth loss in a mammal is known in the literature, see Rodan, G. A. et al., "Therapeutic Approaches to Bone Diseases," Science Vol 289, 1 Sep. 2000 pp. 1508-14.

Another embodiment of the invention is a method of treating of preventing Paget's disease in a mammal in need thereof by administering to the mammal a therapeutically effective amount of any of the compounds or pharmaceutical compositions described above. The use of SERMs to treat Paget's disease in a mammal is known in the literature, see Rodan, G. A. et al., "Therapeutic Approaches to Bone Diseases," Science Vol 289, 1 Sep. 2000 pp. 1508-14.

Another embodiment of the invention is a method of treating or preventing uterine fibroid disease in a mammal in need thereof by administering to the mammal a therapeutically effective amount of any of the compounds or pharmaceutical compositions described above. The use of SERMS to treat uterine fibroids, or uterine leiomyomas, is known in the literature, see Palomba, S., et al, "Effects of raloxifene treatment on uterine leiomyomas in postmenopausal women," Fertil Steril. 2001 July; 76(1):38-43.

Another embodiment of the invention is a method of treating or preventing obesity in a mammal in need thereof by administering to the mammal a therapeutically effective amount of any of the compounds or pharmaceutical compositions described above. The use of SERMs to treat obesity is known in the literature, see Picard, F. et al., "Effects of the estrogen antagonist EM-652. HCl on energy balance and lipid metabolism in ovariectomized rats," Int J Obes Relat Metab Disord. 2000 July; 24(7):830-40.

Another embodiment of the invention is a method of treating or preventing cartilage degeneration, rheumatoid arthritis or osteoarthritis in a mammal in need thereof by administering to the mammal a therapeutically effective amount of any of the compounds or pharmaceutical compositions described above. The use of SERMs to treat cartilage degeneration, rheumatoid arthritis or osteoarthritis is known in the literature, see Badger, A. M. et al., "Idoxifene, a novel selective estrogen receptor modulator, is effective in a rat model of adjuvant-induced arthritis." J Pharmacol Exp Ther. 1999 December; 291(3): 1380-6.

Another embodiment of the invention is a method of treating or preventing endometriosis in a mammal in need thereof by administering to the mammal a therapeutically effective amount of any of the compounds or pharmaceutical compositions described above. The use of SERMs to treat endometriosis is known in the art, see Steven R. Goldstein, "The Effect of SERMs on the Endometrium," Annals of the New York Academy of Sciences 949:237-242 (2001).

Another embodiment of the invention is a method of treating or preventing urinary D incontinence in a mammal in need thereof by administering to the mammal a therapeutically effective amount of any of the compounds or pharmaceutical compositions described above. The use of SERMs to treat urinary incontinence is known in the art, see, Goldstein, S. R., "Raloxifene effect on frequency of surgery for pelvic floor relaxation," Obstet Gynecol. 2001 July; 98(1):91-6.

Another embodiment of the invention is a method of treating or preventing cardiovascular disease, restenosis, lowering levels of LDL cholesterol and inhibiting vascular smooth muscle cell proliferation in a mammal in need thereof by administering to the mammal a therapeutically effective amount of any of the compounds or pharmaceutical compositions described above. Estrogen appears to have an effect on the biosynthesis of cholesterol and cardiovascular health. Statistically, the rate of occurrence of cardiovascular disease is roughly equal in postmenopausal women and men; however, premenopausal women have a much lower incidence of cardiovascular disease than men. Because postmenopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol. The utility of SERMs in treating or preventing cardiovascular disease, restenosis, lowering levels of LDL cholesterol and inhibiting vascular smooth muscle cell proliferation is known in the art, see Nuttall, M E et al., "Idoxifene: a novel selective estrogen receptor modulator prevents bone loss and lowers cholesterol levels in ovariectomized rats and decreases uterine weight in intact rats," Endocrinology 1998 December; 139(12):5224-34; Jordan, V. C. et al., "Selective estrogen receptor modulation and reduction in risk of breast cancer, osteoporosis and coronary heart disease," Natl Cancer Inst 2001 October; 93(19): 1449-57; Guzzo J A., "Selective estrogen receptor modulators—a new age of estrogens in cardiovascular disease?," Clin Cardiol 2000 January; 23(1): 15-7; Simoncini T, Genazzani A R., "Direct vascular effects of estrogens and selective estrogen receptor modulators," Curr Opin Obstet Gynecol 2000 June; 12(3):181-7.

Another embodiment of the invention is a method of treating or preventing the impairment of cognitive functioning, age-related mild cognitive impairment or cerebral degenerative disorders in a mammal in need thereof by administering to the mammal a therapeutically effective amount of any of the compounds or pharmaceutical compositions described above. In models, estrogen has been shown to have beneficial effects on cognitive functioning, such as relieveing anxiety and depression and treating or preventing Alzheimer's disease. Estrogen affects the central nervous system by increasing cholinergic functioning, neurotrophin and neurotrophin receptor expression. Estrogen also increases glutamergic synaptic transmission, alters amyloid precursor protein processing and provides neuroprotection. Thus, the estrogen receptor modulators of the present invention could be beneficial for improving cognitive functioning or treating age-related mild cognitive impairment, attention deficit disorder, sleep disorders, irritability, impulsivity, anger management, multiple sclerosis and Parkinsons disease. See, Sawada, H and Shimohama, S, "Estrogens and Parkinson disease: novel approach for neuroprotection," *Endocrine.* 2003 June; 21(1):77-9; McCullough L D, and Hurn, P D, "Estrogen and ischemic neuroprotection: an integrated view," *Trends Endocrinol Metab.* 2003 July; 14(5):228-35; which are hereby incorporated by reference in their entirety. The utility of SERMs to prevent the impairment of cognitive functioning is known in the art, see Yaffe, K., K. Krueger, S. Sarkar, et al. 2001. Cognitive function in postmenopausal women treated with raloxifene. N. Eng. J. Med. 344: 1207-1213.

Another embodiment of the invention is a method of treating or preventing depression in a mammal in need thereof by administering to the mammal a therapeutically effective amount of any of the compounds or pharmaceutical compositions described above. The utility of estrogens to prevent depression has been described in the art, see Carranza-Liram S., Valentino-Figueroa M L, "Estrogen therapy for depression in postmenopausal women." Int J Gynnaecol Obstet 1999 April; 65(1):35-8. Specifically, estrogen receptor beta (ERβ) selective agonists would be useful in the treatment of anxiety or depressive illness, including depression, perimenopausal depression, post-partum depression, premenstrual syndrome, manic depression, anxiety, dementia, and obsessive compulsive behavior, as either a single agent or in combination with other agents. Clinical studies have demonstrated the efficacy of the natural estrogen, 17β-estradiol, for the treatment of various forms of depressive illness, see Schmidt P J, Nieman L, Danaceau M A, Tobin M B, Roca C A, Murphy J H, Rubinow D R. Estrogen replacement in perimenopause-related depression: a preliminary report. *Am J Obstet Gynecol* 183:414-20, 2000; and Soares C N, Almeida O P, Joffe H, Cohen L S. Efficacy of estradiol for the treatment of depressive disorders in perimenopausal women: a double-blind, randomized, placebo-controlled trial. *Arch Gen Psychiatry,* 58:537-8, 2001; which are hereby incorporated by reference. Bethea et al (Lu N Z, Shlaes T A, Gundlah C, Dziennis S E, Lyle R E, Bethea C L. Ovarian steroid action on tryptophan hydroxylase protein and serotonin compared to localization of ovarian steroid receptors in midbrain of guinea pigs. *Endocrine* 11:257-67, 1999, which is hereby incorporated by reference, have suggested that the anti-depressant activity of estrogen may be mediated via regulation of serotonin synthesis in the serotonin containing cells concentrated in the dorsal raphe nucleus.

Another embodiment of the invention is a method of treating or preventing anxiety in a mammal in need thereof by administering to the mammal a therapeutically effective amount of any of the compounds or pharmaceutical compositions described above. The contribution of estrogen receptors in the modulation of emotional processes, such as anxiety has been described in the art, see Krezel, W., et al., "Increased anxiety and synaptic plasticity in estrogen receptor beta-deficient mice." Proc Natl Acad Sci USA 2001 Oct. 9; 98 (21): 12278-82.

Another embodiment of the invention is a method of treating or preventing inflammation, inflammatory bowel disease or irritable bowel syndrome. Inflammatory bowel diseases, including Crohn's Disease and ulceratie colitis, are chronic disorders in which the intestine (bowel) becomes inflamed, often causing recurring abdominal cramps and diarrhea. The use of estrogen receptor modulators to treat inflammation and inflammatory bowel disease has been described in the art, see Harris, H. A. et al., "Evaluation of an Estrogen Receptor-β Agonist in Animal Models of Human Disease," Endocrinology, Vol. 144, No. 10 4241-4249.

Another embodiment of the invention is a method of treating or preventing hypertension. Estrogen receptor beta has been reported to have a role in the regulation of vascular function and blood pressure, see Zhu, et al, "Abnormal Vacular Function and Hypertension in Mice Deficient in Estrgoen Receptor β," *Science*, Vol 295, Issue 5554, 505-508, 18 Jan. 2002.

Another embodiment of the invention is a method of treating or preventing sexual dysfunction in males or females. The use of estrogen receptor modulators to treat sexual dysfunction has been described in the art, see Baulieu, E. et al,, "Dehydroepiandrosterone (DHEA), DHEA sulfate, and aging: Contribution of the DHEAge Study to a scociobiomedical issue," PNAS, Apr. 11, 2000, Vol. 97, No. 8, 4279-4282; Spark, Richard F., "Dehydroepiandrosterone: a springboard hormone for female sexuality," *Fertility and Sterility*, Vol. 77, No. 4, Suppl 4, April 2002, S19-25.

Another embodiment of the invention is a method of treating or preventing retinal degeneration. Estrogen has been shown to have a beneficial effect of reducing the risk of advanced types of age-reated maculopathy, see Snow, K. K., et al., "Association between reproductive and hormonal factors and age-related maculopathy in postmenopausal women," *Americal Journal of Ophthalmology*, Vol. 134, Issue 6, December 2002, pp. 842-48.

Exemplifying the invention is the use of any of the compounds described above in the preparation of a medicament for the treatment or prevention of bone loss, bone fractures, osteoporosis, metastatic bone disease, Paget's disease, periodontal disease, cartilage degeneration, endometriosis, uterine fibroid disease, hot flashes, cardiovascular disease, impairment of cognitive functioning, cerebral degenerative disorders, restenosis, gynecomastia, vascular smooth muscle cell proliferation, obesity, incontinence, anxiety, depression, perimenopausal depression, post-partum depression, premenstrual syndrome, manic depression, anxiety, dementia, obsessive compulsive behavior, attention deficit disorder, sleep disorders, irritability, impulsivity, anger management, multiple sclerosis and Parkinson's disease, inflammation, inflammatory bowel disease, irritable bowel syndrome, sexual dysfunction, hypertension, retinal degeneration or an estrogen dependent cancer, in a mammal in need thereof.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression resulting from an estrogen deficiency, inflammation, inflammatory bowel disease, irritable bowel syndrome, sexual dysfunction, hypertension, retinal degeneration and cancer, in particular of the breast, uterus and prostate. Combinations of the presently disclosed compounds with other agents useful in treating or preventing the disorders disclosed herein are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; selective serotonin reuptake inhibitors (SSRIs); an aromatase inhibitor; and the pharmaceutically acceptable salts and mixtures thereof. A preferred combination is a compound of the present invention and an organic bisphosphonate. Another preferred combination is a compound of the present invention and a cathepsin K inhibitor. Another preferred combination is a compound of the present invention and an estrogen. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

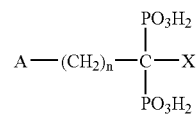

wherein n is an integer from 0 to 7 and wherein A and X are independently selected from the group consisting of H, OH, halogen, $NH_2$, SH, phenyl, $C_{1-30}$ alkyl, $C_{3-30}$ branched or cycloalkyl, bicyclic ring structure containing two or three N, $C_{1-30}$ substituted alkyl, $C_{1-10}$ alkyl substituted $NH_2$, $C_{3-10}$ branched or cycloalkyl substituted $NH_2$, $C_{1-10}$ dialkyl substituted $NH_2$, $C_{1-10}$ alkoxy, $C_{1-10}$ alkyl substituted thio, thiophenyl, halophenylthio, $C_{1-10}$ alkyl substituted phenyl, pyridyl, furanyl, pyrrolidinyl, imidazolyl, imidazopyridinyl, and benzyl, such that both A and X are not selected from H or OH when n is O; or A and X are taken together with the carbon atom or atoms to which they are attached to form a $C_{3-10}$ ring.

In the foregoing chemical formula, the alkyl groups can be straight, branched, or cyclic, provided sufficient atoms are selected for the chemical formula. The $C_{1-30}$ substituted alkyl can include a wide variety of substituents, nonlimiting examples which include those selected from the group consisting of phenyl, pyridyl, furanyl, pyrrolidinyl, imidazonyl, $NH_2$, $C_{1-10}$ alkyl or dialkyl substituted $NH_2$, OH, SH, and $C_{1-10}$ alkoxy.

The foregoing chemical formula is also intended to encompass complex carbocyclic, aromatic and hetero atom structures for the A or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_{1-30}$ alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated.

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. For humans, an effective oral dose of bisphosphonate is typically from about 1.5 to about 6000 µg/kg body weight and preferably about 10 to about 2000 µg/kg of body weight. In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week. The bisphosphonates may also be administered monthly, ever six months, yearly or even less frequently, see WO 01/97788 (published Dec. 27, 2001) and WO 01/89494 (published Nov. 29, 2001).

"Estrogen" includes, but is not limited to naturally occurring estrogens [7-estradiol ($E_2$), estrone ($E_1$), and estriol ($E_3$)], synthetic conjugated estrogens, oral contraceptives and sulfated estrogens. See, Gruber C J, Tschugguel W, Schneeberger C, Huber J C., "Production and actions of estrogens" N Engl J Med 2002 Jan. 31; 346(5):340-52.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Cathepsin K inhibitors" refers to compounds which interfere with the activity of the cysteine protease cathepsin K. Nonlimiting examples of cathepsin K inhibitors can be found in PCT publications WO 00/55126 to Axys Pharmaceuticals and WO 01/49288 to Merck Frosst Canada & Co. and Axys Pharmaceuticals.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HIG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR® see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL® see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL® see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89

(5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

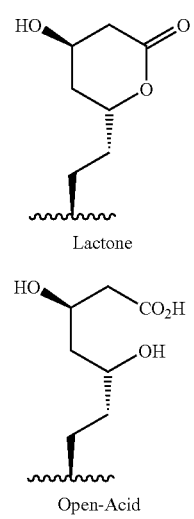

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically-acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not-limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

Calcitonin is a 32 amino acid pepetide produced primarily by the thyroid which is known to participate in calcium and phosphorus metabolism. Calcitonin suppresses resorption of bone by inhibiting the activity of osteoclasts. Thus, calcitonin can allow osteoblasts to work more effectively and build bone.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OR) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be reponsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, $3^{rd}$ ed., 990-1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

Selective Serotonin Reuptake Inhibitors act by increasing the amount of serotonin in the brain. SSRIs have been used successfully for a decade in the United States to treat depression. Non-limiting examples of SSRIs include fluoxetine, paroxetine, sertraline, citalopram, and fluvoxanine. SSRIs are also being used to treat disoreders realted to estrogen functioning, suchs as premenstrual syndrome and premenstrual dysmorphic disorder. See Sundstrom-Poromaa I, Bixo M, Bjorn I, Nordh O., "Compliance to antidepressant drug therapy for treatment of premenstrual syndrome," J Psychosom Obstet Gynaecol 2000 December; 21(4):205-11.

As used herein the term "aromatase inhibitor" includes compounds capable of inhibiting aromatase, for example commercially available inhibitors such as: aminoglutemide (CYTANDREN®), Anastrazole (ARIMIDEX®), Letrozole (FEMARA®), Formestane (LENATRON®), Exemestane (AROMASIN®), Atamestane (1-methylandrosta-1,4-diene-3,17-dione), Fadrozole (4-(5,6,7,8-Tetrahydroimidazo[1,5-a]pyridin-5-yl)-benzonitrile, monohydrochloride), Finrozole (4-(3-(4-Fluorophenyl)-2-hydroxy-1-(1H-1,2,4-triazol-1-yl)-propyl)-benzonitrile), Vorozole (6-[(4-chlorophenyl)-1H-1,2,4-triazol-1-ylmethyl]-1-methyl-1H-benzotriazole), YM-511 (4-[N-(4-bromobenzyl)-N-(4-cyanophenyl)amino]-4H-1,2,4-triazole) and the like.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The present invention also encompasses a pharmaceutical composition useful in the treatment of the diseases mentioned herein, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; an aromatase inhibitor; and the pharmaceutically acceptable salts and mixtures thereof.

These and other aspects of the invention will be apparent from the teachings contained herein.

DEFINITIONS

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The term "alkyl" shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc.).

The term "alkenyl" shall mean a substituting univalent group derived by conceptual removal of one hydrogen atom from a straight or branched-chain acyclic unsaturated hydrocarbon (i.e., —CH=$CH_2$, —CH=$CHCH_3$, —C=$C(CH_3)_2$, —$CH_2$CH=$CH_2$, etc.).

The term "alkynyl" shall mean a substituting univalent group derived by conceptual removal of one hydrogen atom from a straight or branched-chain acyclic unsaturated hydrocarbon containing a carbon-carbon triple bond (i.e., —C≡CH, —C≡—$CCH_3$, —C≡$CCH(CH_3)_2$, —$CH_2$C≡CH, etc.).

The term "alkylidene" shall mean a substituting bivalent group derived from a straight or branched-chain acyclic saturated hydrocarbon by conceptual removal of two hydrogen atoms from the same carbon atom (i.e., =$CH_2$, =$CHCH_3$, =$C(CH_3)_2$, etc.).

The term "cycloalkyl" shall mean a substituting univalent group derived by conceptual removal of one hydrogen atom from a saturated monocyclic hydrocarbon (i.e., cyclopropyl, cyclobutyl, cyclopentyl, cyclohexyl, or cycloheptyl).

The term "aryl" as used herein refers to a substituting univalent group derived by conceptual removal of one hydrogen atom from a monocyclic or bicyclic aromatic hydrocarbon. Examples of aryl groups are phenyl, indenyl, and naphthyl.

The term "heteroaryl" as used herein refers to a substituting univalent group derived by the conceptual removal of one hydrogen atom from a monocyclic or bicyclic aromatic ring system containing 1, 2, 3, or 4 heteroatoms selected from N, O, or S. Examples of heteroaryl groups include, but are not limited to, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, and purinyl. Heteraryl substituents can be attached at a carbon atom or through the heteroatom.

The term "halo" shall include iodo, bromo, chloro and fluoro.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The present invention also includes protected derivatives of compounds disclosed herein. For example, when compounds of the present invention contain groups such as hydroxyl or carbonyl, these groups can be protected with a suitable protecting group. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of the present invention can be prepared by methods well known in the art.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

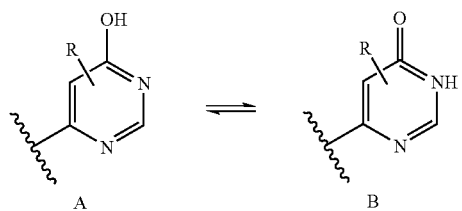

When any variable (e.g. $R^1$, $R^2$, $R^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

In choosing compounds of the present invention, one of ordinary skill in the art will recognize that the various substituents, i.e. $R^1$, $R^2$ and $R^3$ are to be chosen in conformity with well-known principles of chemical structure connectivity.

Representative compounds of the present invention typically display submicromolar affinity for alpha and/or beta estrogen receptors, and preferably agonize the beta estrogen receptor. Compounds of this invention are therefore useful in treating mammals suffering from disorders related to estrogen functioning.

The compounds of the present invention are available in racemic form or as individual enantiomers. For convenience, some structures are graphically represented as a single enantiomer but, unless otherwise indicated, is meant to include both racemic and enantiomerically pure forms. Where cis and trans sterochemistry is indicated for a compound of the present invention, it should be noted that the stereochemistry should be construed as relative, unless indicated otherwise. For example, a (+) or (−) designation should be construed to represent the indicated compound with the absolute stereochemistry as shown.

Racemic mixtures can be separated into their individual enantiomers by any of a number of conventional methods. These include, but are not limited to, chiral chromatography, derivatization with a chiral auxiliary followed by separation by chromatography or crystallization, and fractional crystallization of diastereomeric salts. Deracemization procedures may also be employed, such as enantiomeric protonation of a pro-chiral intermediate anion, and the like.

The fused five-membered triazole ring contains three nitrogen atoms, and thus tautomeric ($R^2$ is hydrogen) and positional ($R^2$ is a non-hydrogen group) isomers are possible. These isomeric forms, as shown below, are contemplated to fall within the scope of the present invention:

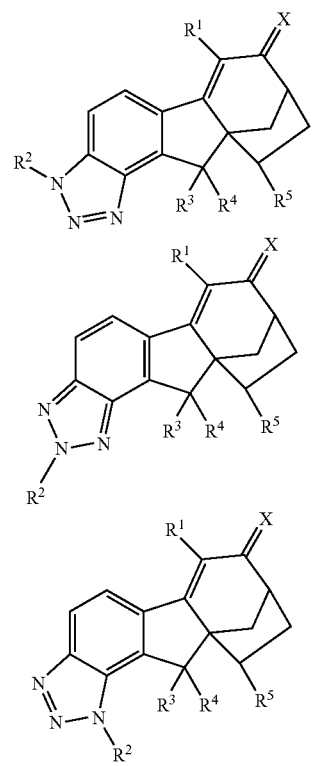

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

In the schemes and examples below, various reagent symbols and abbreviations have the following meanings:

AcOH: Acetic Acid
AgOAc: Silver acetate
$AlCl_3$: Aluminum chloride
AIBN: 2,2-azobisisobutyronitrile
$BBr3$: Boron Tribromide
$BnNH_2$: Benzylamine
$BrCH_2CH_2F$: 1-Bromo-2-fluoroethane
$BrCH_2CH_2OBn$: 1-Bromo-2-benzyloxyethane
$CCl_4$: Carbon tetrachloride
$CH_2Cl_2$: Dichloromethane
CuBr: Copper Bromide
CuCN: Copper cyanide
CuI: Copper Iodide
DBU: 1,8-diazabicyclo[5.4.0]undec-7-ene
DBN: 1,5-diazabicyclo[4.3.0]non-5-ene
DIEA: N,N-Diisopropylethylamine
DMAC: N,N-Dimethylacetamide
DMAP: 4-(Dimethylamino)pyridine
DMF: Dimethylformamide
EtOH: Ethanol
$Et_3N$: Triethylamine
EtSH: ethanethiol
EVK: Ethyl vinyl ketone
HCl: Hydrochloric acid
HOAc: Acetic Acid
$K_2CO_3$: Potassium carbonate
KI: Potassium iodide
$KN(TMS)_2$: Potassium bis(trimethylsilyl)amide
LiCl: Lithium chloride
LDA: Lithium Dimethylamide
$LiN(TMS)_2$: Lithium bis(trimethylsilyl)amide
$Me_2CO_3$: Methyl carbonate
MeCN: Methyl cyanide MeOH: Methanol
MFSDA: methyl(fluorosulfonyl)difluoroacetate
MsCl: Mesyl chloride
MVK: Methyl vinyl ketone
NaH: Sodium hydride
NaI: Sodium iodide
$NaNO_2$: Sodium nitrite
NaOH: Sodium hydroxide
NaOMe: Sodium methylate
NaOt-Bu: Sodium t-butoxide
NCCO2Et: Ethyl cyanoformate
NBS: N-Bromo Succinimide
NCS: N-Chloro Succinimide
NIS: N-IodoSuccinimide
NMO: N-methylmorpholine N-oxide
NMP: M-Methyl-2-pyrrolidone
$PdCl_2(PPh_3)_2$: Bis(triphenylphosphine)palladium(II) chloride
$PdCl2(dppf).CH_2Cl_2$: [1,1'-Bis(diphenylphosphino)ferrocene]dichloropalladium (II)
$Pd_2(dba)_3$: Tris(dibenzylideneacetone)dipalladium (0)
$Pd(OAc)_2$: Palladium acetate
$Pd(PPh_3)_4$: Tetrakis(triphenylphosphine)palladium(0)
$PhB(OH)_2$: Phenyl boronic acid
$PhCH_3$: Toluene
PhH: Benzene
PhMe: Toluene
PMB-Cl: Paramethoxybenzyl chloride
SEM-Cl: 2-(Trimethylsilyl)ethoxymethyl chloride
$SMe_2$: Dimethyl sulfide
$SnMe_4$: Tetramethyltin
$Tf_2O$: Triflic anhydride
TBF: Tetrahydrofuran
TsOH: p-Toluenesulfonic acid
TPAP: Tripropylammonium perruthenate
XANTPHOS: 4,5-bis(diphenylphosphino)-9,9-dimethylxanthene The novel compounds of the present invention can be prepared according to the procedures of the following schemes and examples, using appropriate materials, and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The compounds of the present invention are prepared according to the general methods outlined in Schemes I-XI. In these schemes, $R^I$ represents $R^1$ or a precursor thereof; $R^{Ia}$ and $R^{Ib}$ represent non-hydrogen values of $R^1$, or precursors thereof; $R^{II}$ represents $R^5$ or a precursor thereof; $R^{IIIa}$ and $R^{IIIb}$ represent non-hydrogen values of $R^3$ and/or $R^4$, or precursors thereof; RIV represents $OR^a$ and $NR^aR^a$; $R^V$ represents hydrogen, a $C_{1-5}$ alkyl group or a substituted $C_{1-5}$ alkyl group; $R^O$ and $R^P$ independently represent hydrogen or an N-protecting group for an aniline nitrogen such as acetyl or benzyl; $R^M$ represents a carboxyl esterifying group such as methyl, ethyl, allyl or benzyl; $R^Q$ represents hydrogen or a N-protecting group for a benzotriazole group; $R^N$ represents hydrogen or a removable protecting group for a phenolic hydroxyl such as methyl, methoxymethyl or benzyl; $R^F$ represents methyl, trifluoromethyl, nonafluorobutyl, phenyl or tolyl; Y represents a displaceable leaving group such as fluoro, chloro, bromo, iodo, methanesulfonyloxy, p-toluenesulfonyloxy, trifluoromethylsulfonyloxy and the like or a precursor thereof such as hydroxyl, benzyloxy or acetoxy; and Z represents hydrogen or a removable aryl blocking group such as chloro or bromo. Other R groups are defined in the schemes in which they appear.

The final compounds of the present invention are synthesized from substituted indanone compounds which are prepared by the methods outlined in Schemes I-IV. The starting materials for the synthesis of Scheme I are 5-amino-1-indanone derivatives (1), which are either known compounds or are prepared by conventional methods known in the art. In step 1 of Scheme I, a protected 5-amino-1-indanone (1) is reacted with a carboxylating reagent such as ethyl cyanoformate or ethyl chloroformate in the presence of base to provide the beta-ketoester (2). In step 2, the beta-ketoester (2) is then reacted with an alkylating agent L-CH$_2$CH$_2$—Y, where L represents a displaceable leaving group, in the presence of a base to give intermediate (3). In the case where Y also represents a displaceable leaving group, the relative reactivities of the two groups are appropriately chosen so that L is the more easily displaced group. In step 3, the carboxyl group of intermediate (3) is removed by hydrolysis or other cleavage of the ester followed by decarboxylation to give (4). Step 4 represents an alternative introduction of the moiety —CH$_2$CH$_2$—Y. In this case the substitution is accomplished by a reductive alkylation reaction wherein (1) is reacted with a substituted aldehyde Y—CH$_2$CHO under basic conditions followed by hydrogenation of the resulting alkylidene intermediate. In this instance Y is most appropriately a precursor group which can be converted to a displaceable leaving group at a later point in the synthesis. Alternatively, introduction of the moiety —CH$_2$CH$_2$—Y can be accomplished by reacting indanone (1) with an alkylating agent L-CH$_2$CH$_2$—Y, where L represents a displaceable leaving group, in the presence of a base to give (4). In the case where Y also represents a displaceable leaving group, the relative reactivities of the two groups are appropriately chosen so that L is the more easily displaced group.

SCHEME I

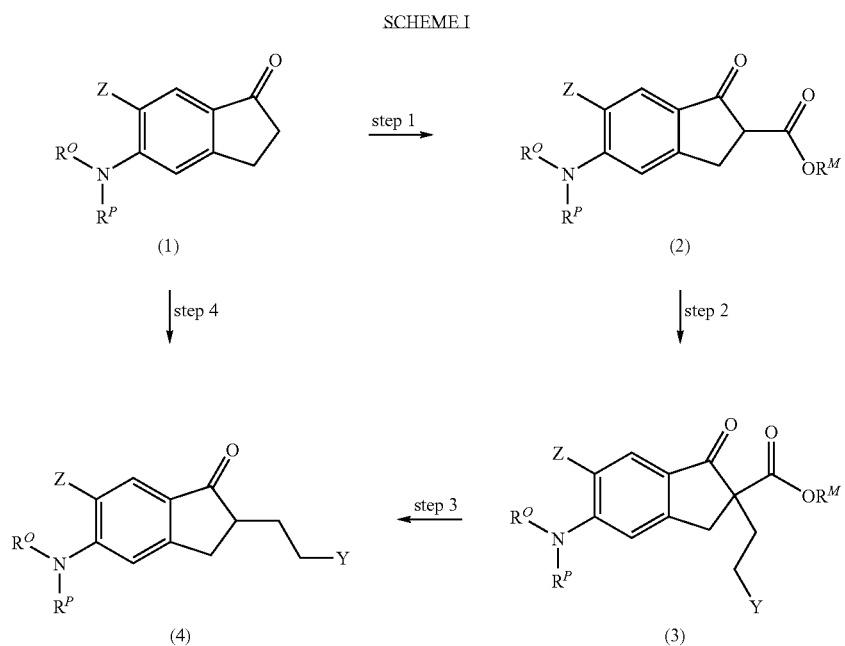

Representative reagents and reaction conditions indicated in Scheme I as steps 1-4 are as follows:

| Step 1 | i) LiN(TMS)$_2$, THF, −78 to 40° C. | $R^M$ = Et |
|---|---|---|
|  | ii) NCCO$_2$Et, −78° C. to rt |  |
|  | Me$_2$CO$_3$, NaH, PhH, 60° C. | $R^M$ = Me |
| Step 2 | BrCH$_2$CH$_2$F, K$_2$CO$_3$, KI, DMAC, 65° C. | Y = F |
|  | BrCH$_2$CH$_2$OBn, K$_2$CO$_3$, KI, DMAC, 60-100° C. | Y = OBn |
| Step 3 | NaOH, H$_2$O, MeOH, THF 0 to 40° C. or |  |
|  | 6 N HCl, HOAc, 90-100° C., |  |
| Step 4 | BnOCH$_2$CHO, NaOMe, MeOH, H$_2$, Pd/C | Y = OBn |
|  | (HOCH$_2$CHO)$_2$, NaOMe, MeOH, H$_2$, Pd/C | Y = OH |

The synthesis of Scheme II is analogous to that of Scheme I but starts with 5-alkoxy-1-indanones (5) to prepare 2-substituted-5-alkoxy-1-indanones (8). The 5-alkoxy-1-indanone starting materials for Scheme 2 are either known compounds or can be prepared by conventional methods known in the art.

SCHEME II

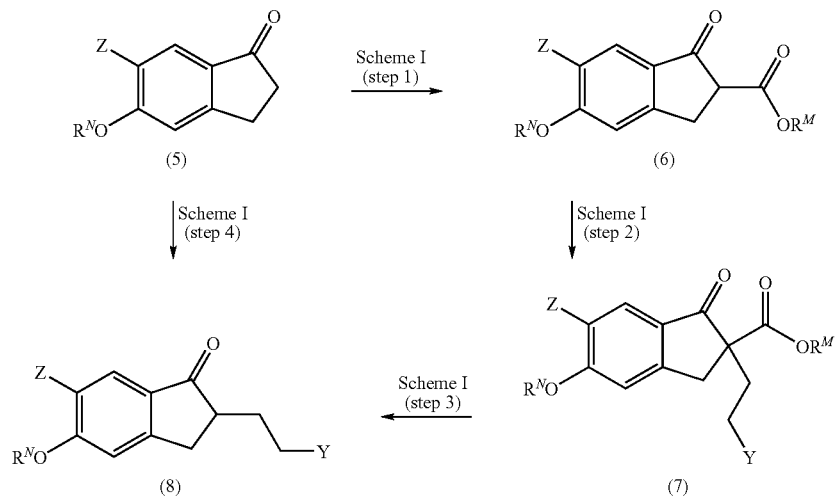

Scheme III describes the synthesis of triazolo-indanones (13), which are the starting materials for Scheme IV. The starting materials for the synthesis of Scheme III are protected 5-amino-1-indanone derivatives (1a), which are either known compounds or are prepared by conventional methods known in the art. In step 1 of Scheme III, compound (1a) is nitrated by conventional means to provide nitro compound (9). Removal of the protecting group $R^O$ from (9) in step 2 yields the nitro-aniline derivative (10). In step 3, reduction of the nitro group of (10) provides the diamino compound (11). Diazotization (step 4) of the 4,5-diamino-indanone (11) produces the triazolo-indanone (12). The fused triazole ring of (12) is N-protected using any of a number of well known groups represented by $R^Q$. Since the fused heteroaryl ring contains three nitrogen atoms, positional isomers as indicated by the structures (13a), (13b) and (13c) are possible. These isomers can be used as mixtures or they can be separated and used independently in the following steps. Structure (13) represents these possibilities.

SCHEME III

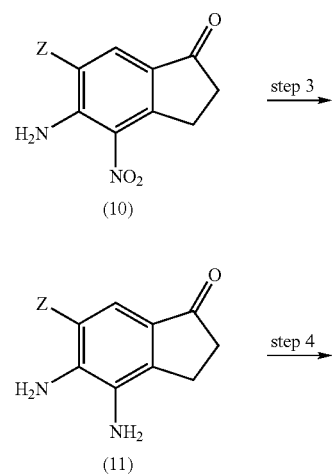

-continued

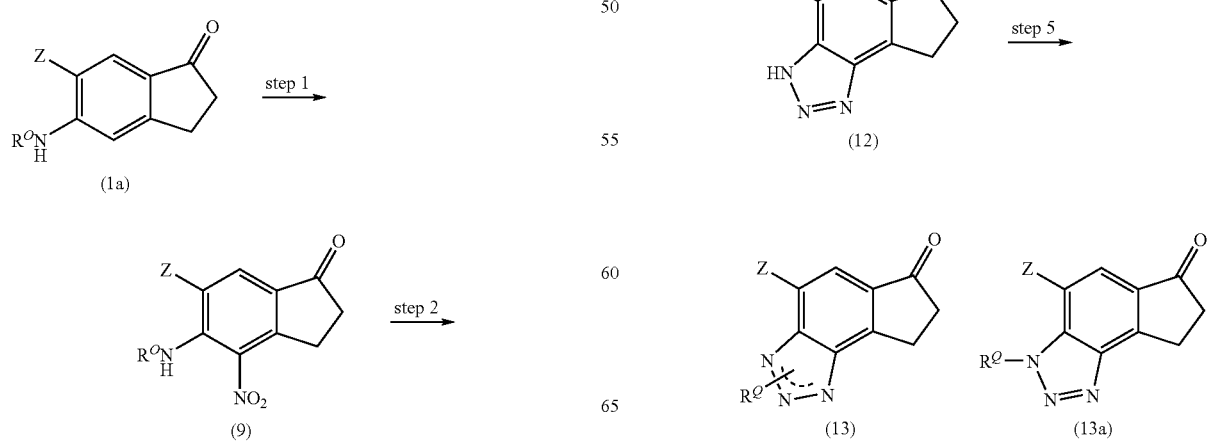

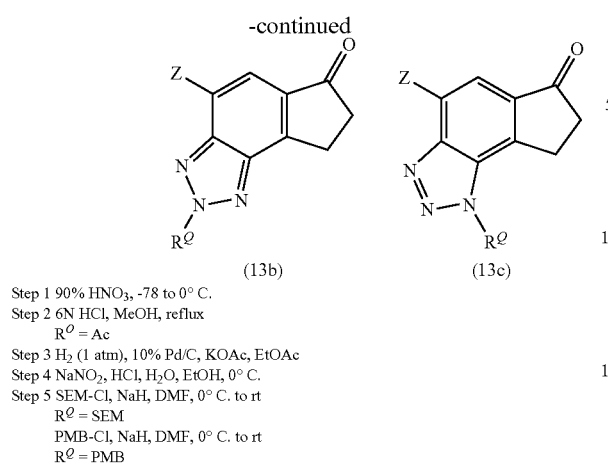

Step 1 90% HNO₃, −78 to 0° C.
Step 2 6N HCl, MeOH, reflux
   R^O = Ac
Step 3 H₂ (1 atm), 10% Pd/C, KOAc, EtOAc
Step 4 NaNO₂, HCl, H₂O, EtOH, 0° C.
Step 5 SEM-Cl, NaH, DMF, 0° C. to rt
   R^Q = SEM
   PMB-Cl, NaH, DMF, 0° C. to rt
   R^Q = PMB The synthesis of Scheme IV is analogous to that of Scheme I but starts with triazolo-indanones (13) to produce 2-substituted-4,5-triazol-1-indanones (17). The triazolo-indanones (13) are prepared according to Scheme III.

leaving group may be required prior to or in conjunction with this step. Step 4 is an optional protection, deprotection, or deprotection-reprotection step of the nitrogen which may be carried-out on compound (20) to give intermediate (21) depending on the desired $R^O$ group. In the case where $R^I$=H in intermediate (21), a variety of non-hydrogen $R^I$ groups can be introduced at this point in the synthesis as described further below in Scheme VIII. In step 5, indanone (21) undergoes nitration to produce (22). When compound (21) possesses an unsubstituted 6-position (Z=H), a regioisomeric nitro compound may also form which can be separated from the desired product by conventional means, for example chromatography or crystallization. Reduction of the nitro group of (22) in step 6 yields the amino compound (23). In step 7, diazotization of (23) provides the triazolo compound (24). In the case where Z represents a non-hydrogen aryl blocking group in intermediate (24), it is removed in step 8 to provide the final compound (25). In the case where $R^O$ is a protecting group, a deprotection step may precede, accompany, or follow the removal of Z.

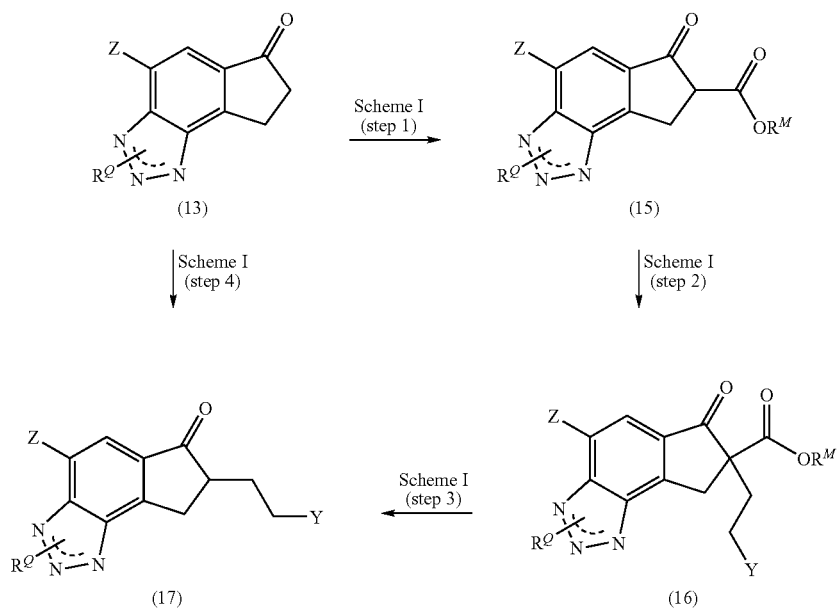

Scheme V illustrates a method for constructing the pentacyclic 3,9,10,11-tetrahydro-8,10a-methanocyclohepta[1,2]indeno[4,5-d][1,2,3]triazol-7(8H)-one compounds of the present invention. In step 1, the 2-substituted-1-indanone (4) reacts with a vinyl ketone in the presence of base to give the diketone (18). The diketone is then cyclized (step 2) under basic or acidic conditions to provide the tetrahydrofluorenone product (19). In step 3, the ethylidene bridge is formed by an internal alkylation reaction in the presence of a base and/or with heating to produce (20). Conversion of Y to a reactive

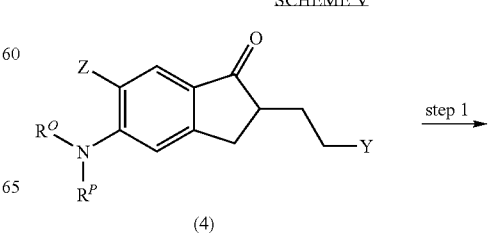

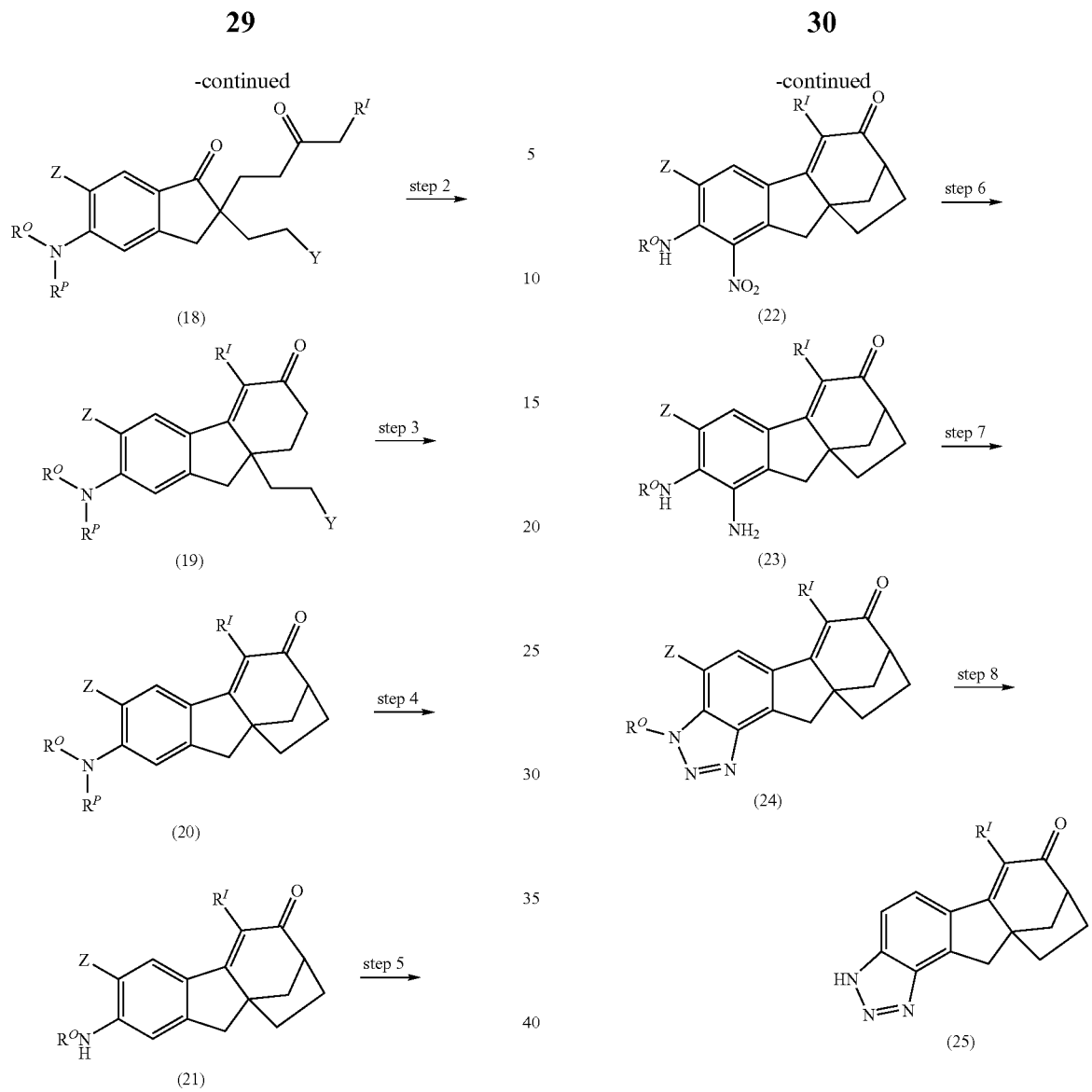

Representative reagents and reaction conditions indicated in Scheme V as steps 1-8 are as follows:

| Step 1 | MVK, NaOMe, MeOH, rt to 60° C. or | $R^I$ = H |
|---|---|---|
| | MVK, DBN, THF, rt to 60° C. | |
| | EVK, NaOMe, MeOH, rt to 60° C. | $R^I$ = Me |
| Step 2 | pyrrolidine, HOAc, PhMe, 60-85° C. or | |
| | NaOH, H₂O, MeOH or EtOH, rt to 85° C. or | |
| | 6 N HCl, HOAc, 90-100° C. or | |
| | TsOH—H₂O, PhMe, 60-100° C. | |
| Step 3 | LiCl, DMF, 150° C. | Y = F |
| | i) BBr₃, CH₂Cl₂, −78° C. | Y = F |
| | ii) KN(TMS)₂, THF, −78° C. | |
| | pyridine-HCl, 190° C. | Y = OBn |
| | i) NaOMe, MeOH | Y = OAc |
| | ii) MsCl, Et₃N, CH₂Cl₂ | |
| | iii) LDA, THF, −78° C. to rt | |
| Step 4 | i) pyridine-HCl, 180-195° C. | for $R^O$ = Bn, $R^P$ = Bn |
| | ii) AcCl, K₂CO₃, CH₂Cl₂ | to $R^O$ = Ac, $R^P$ = H |
| Step 5 | 2,3,5,6-tetrabromo-4-methyl-4 nitrocyclohexa-2,5-dienone, | |
| | TFA, rt or NaNO₃, TFA, rt to 80° C. | |
| Step 6 | H₂ (1 atm), 10% Pd/C, KOAc, MeOH, EtOAc | |
| Step 7 | NaNO₂, HCl, H₂O, EtOH, 0° C. | |
| Step 8 | H₂ (1 atm), 20% Pd(OH)₂/C, 5% Pd/CaCO₃, DMF | for Z = Cl |

Scheme VI illustrates an alternative method for constructing the pentacyclic 3,9,10,11-tetrahydro-8,10a-methanocyclohepta[1,2]indeno[4,5-d][1,2,3]triazol-7(8H)-one compounds of the present invention starting with a 2-substituted-5-alkoxy-1-indanone (8) from Scheme II. Steps 1-3 proceed analogously to the corresponding steps in Scheme V to produce the tetrahydrofluorenone (28). In step 4, the protecting group $R^N$ is removed from the phenol hydroxyl. In certain cases, this deprotection will conveniently occur during step 3 rendering a separate deprotection in step 4 unnecessary. Reaction of phenol (29) with a sulfonylating agent in step 5 yields the sulfonate intermediate (30). In step 6, the sulfonate (30) is converted to the aniline derivative (21) in a palladium catalyzed amidation reaction. Such amidation reactions are well known in the art (see for example *J. Am. Chem. Soc.* 2003, 125, 6653-6655; *J. Org. Chem.* 2003, 68, 9563-9573; *J. Org. Chem.* 2000, 65, 1158-1174). Depending on the desired $R^O$ group, a protection, deprotection, or deprotection-reprotection of the nitrogen may be carried-out on compound (21). In the case where $R^I$=H in intermediate (21), a variety of non-hydrogen $R^I$ groups can be introduced at this point in the synthesis as described further below in Scheme VIII. Compound (21) is then converted to the final compound (25) by the methods previously described in Scheme V.

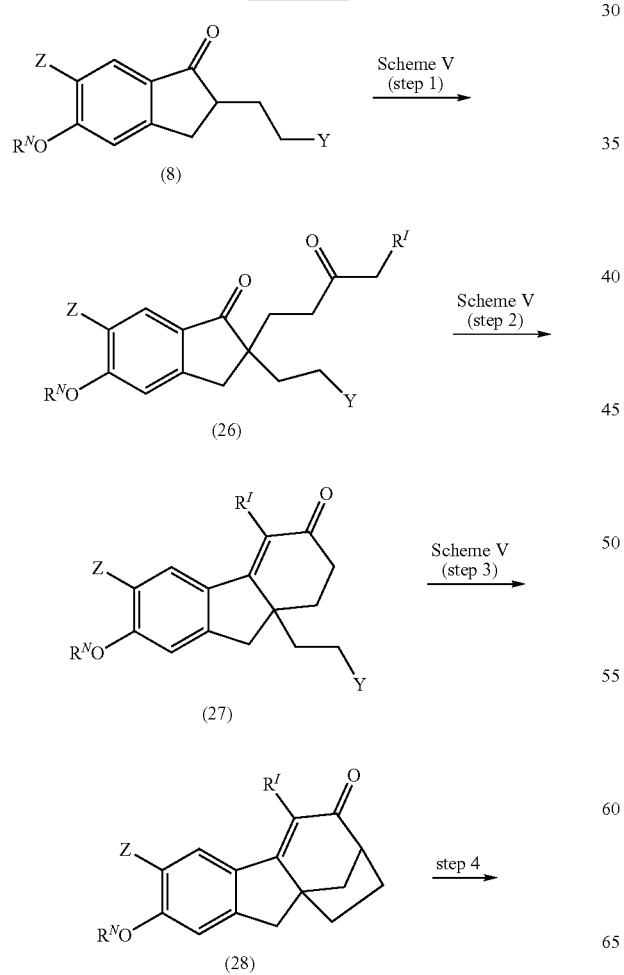

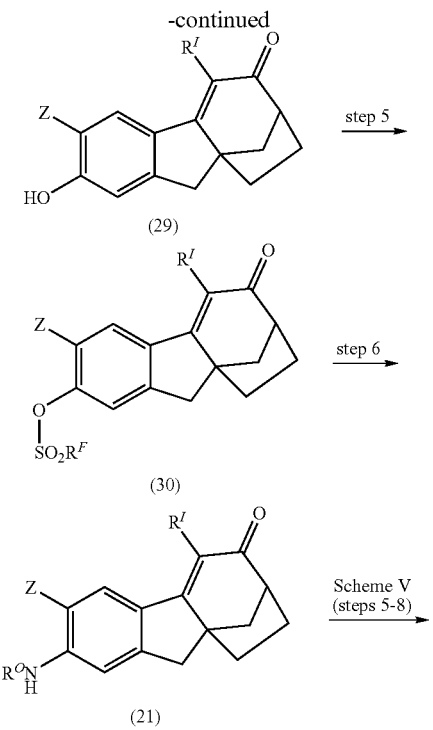

Representative reagents and reaction conditions indicated in Scheme V as steps 4-6 are as follows:

| Step 4 | LiCl, DMF, 150° C. or BBr$_3$, CH$_2$Cl$_2$, -78° C. to rt | $R^N$ = Me |
|---|---|---|
| Step 5 | Tf$_2$O, EtN(i-Pr)$_2$, CH$_2$Cl$_2$, 0° C. to rt | $R^F$ = CF$_3$ |
| Step 6 | Pd$_2$(dba)$_3$, XANTPHOS, Cs$_2$CO$_3$, MeCONH$_2$, PhMe, 80-100° C. | $R^O$ = Ac |
| | Pd(OAc)$_2$, (o-biphenyl)P(t-Bu)$_2$, NaOt-Bu, BnNH$_2$, PhMe, rt to 80° C. | $R^O$ = Bn |
| | Pd(OAc)$_2$, 2-[(Cy)$_2$P]-2',4',6'-[tri-i-Pr]-1,1'-biphenyl K$_2$CO$_3$, PhB(OH)$_2$, H$_2$NCO$_2$t-Bu, t-BuOH, rt to 1 110° C. | $R^O$ = CO$_2$tBu |

Scheme VII illustrates an alternative method for constructing the pentacyclic 3,9,10,11-tetrahydro-8,10a-methanocyclohepta[1,2]indeno[4,5-d][1,2,3]triazol-7(8H)-one compounds of the present invention starting with a 2-substituted-4,5-triazolo-1-indanone (17) from Scheme IV. Steps 1-3 proceed analogously to the corresponding steps in Scheme V to produce the tetrahydrofluorenone (33). In the case where $R^I$=H in intermediate (33), a variety of non-hydrogen $R^I$ groups can be introduced at this point in the synthesis in a manner analogous to that described further below in Scheme VIII. In the case where Z represents a non-hydrogen aryl blocking group in intermediate (33), it is removed in step 4 to provide compound (34). This step proceeds analogously to step 8 in Scheme V. Removal of the $R^Q$ protecting group may precede, accompany, or follow the removal of Z. In Scheme VII the later possibility is illustrated.

SCHEME VII

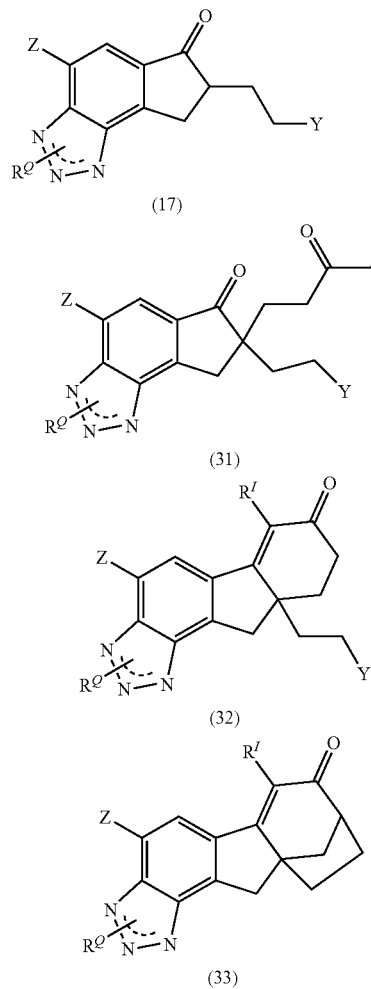

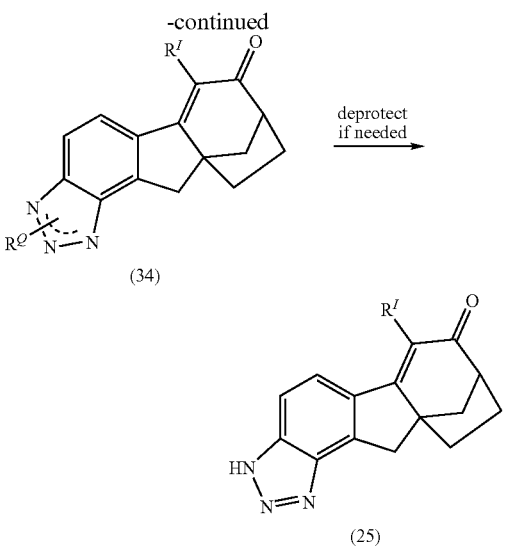

Scheme VIII shows a method for the introduction of a non-hydrogen $R^I$ group onto a C4-unsubstituted ($R^I$=H) tetrahydrofluorenone intermediate (21a), which itself is prepared according to Scheme V or Scheme VI. Enone (21a) undergoes chlorination, bromination, or iodination (step 1) to afford the 4-halo intermediates (21b). Intermediates (21b) are converted by established methods (step 2) into a variety of new derivatives (21c) wherein $R^{Ib}$ is, inter alia, an alkyl, alkenyl, alkynyl, aryl, 10 heteroaryl or arylalkyl group. In certain cases the two steps can be conveniently carried-out in a "one-pot" sequence making the isolation of (21b) unnecessary. If the group $R^{Ib}$ is, or contains, a functional group capable of further modification, such modifications can be carried out to produce additional derivatives. For example, if $R^{Ib}$ is an alkenyl group, it can be reduced by catalytic hydrogenation to an alkyl group. Intermediates (21b) and (21c) are converted to final compounds (25a) and (25b) respectively by the procedures previously described in Scheme V. In an analogous fashion, a non-hydrogen $R^I$ group can be introduced onto a C4-unsubstituted ($R^I$=H) intermediate (33) prepared according to Scheme VII.

SCHEME VIII

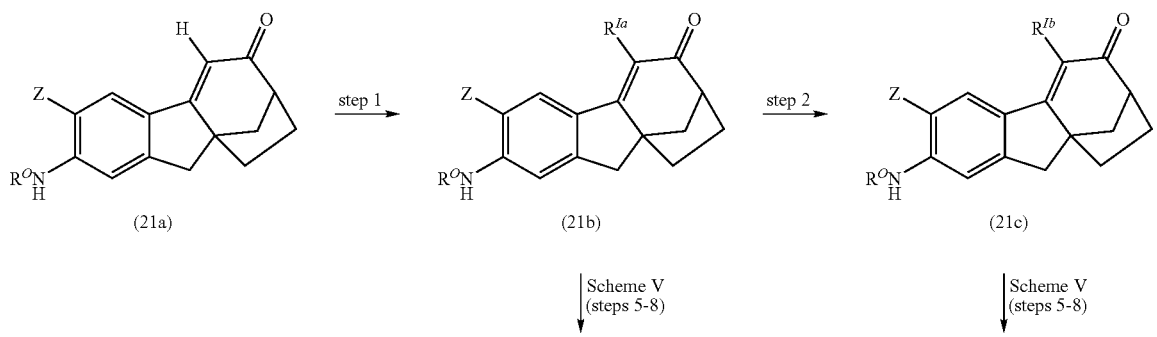

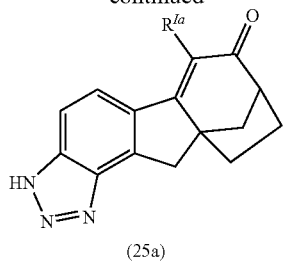

(25a)

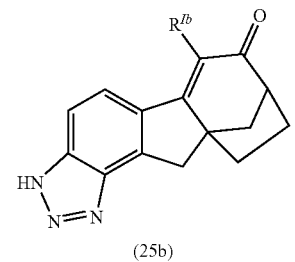

(25b)

Representative reagents and reaction conditions indicated in Scheme V as steps 1-2 are as follows:

| Step 1 | NCS, DMF, rt to 50° C. | $R^{Ia}$ = Cl |
| --- | --- | --- |
| | $Br_2$, $NaHCO_3$, $CH_2Cl_2$ or $CCl_4$, 0° C. to rt or | $R^{Ia}$ = Br |
| | NIS, DMF, 70 to 100° C. or | $R^{Ia}$ = I |
| | $I_2$, $NaHCO_3$, $H_2O$, $CH_2Cl_2$, rt | |
| Step 2 | $FSO_2CF_2CO_2Me$, CuI, EtN(i-Pr)$_2$, DMF, 70 to 100° C. | $R^{Ib}$ = $CF_3$ |
| | $R^{Ib}SnBu_3$, $PdCl_2(PPh_3)_2$, PhMe, 100-110° C. or | $R^{Ib}$ = alkenyl, |
| | $R^{Ib}SnBu_3$, $Pd(PPh_3)_4$, PhMe, 100° C. or | aryl or heteroaryl |
| | $R^{Ib}B(OH)_2$, $PdCl_2(PPh_3)_2$, $Cs_2CO_3$, DMF, 100° C. or | |
| | $R^{Ib}B(OH)_2$, $Pd(PPh_3)_4$, aq $Na_2CO_3$, PhMe, 80° C. | |
| | $(R^{Ib})_3B$, $PdCl_2(dppf)\cdot CH_2Cl_2$, | $R^{Ib}$ = alkyl |
| | $Ph_3As$, $Cs_2CO_3$, $H_2O$, THF, DMF, 60° C. | |
| | $R^{Ib}Sn(CH_2CH_2CH_2)_3N$, $Pd(PPh_3)_4$, | $R^{Ib}$ = alkenyl, |
| | PhMe, 100° C. | alkyl or arylalkyl |
| | CuCN, NMP, 160° C. | $R^{Ib}$ = CN |

Scheme IX illustrates a variation of the syntheses shown in Scheme I and Scheme V which allows for introduction of the $R^{II}$ substituent. In step 1 of Scheme IX indanone (1) is reacted with a substituted aldehyde Y—CH$_2$CHO under basic conditions and the alkylidene intermediate (35) is obtained. This step is similar to step 4 of Scheme I except that the reduction step is omitted. In this instance Y is most appropriately a precursor group which can later be converted to a displaceable leaving group. Introduction of the $R^{II}$ substituent is accomplished in step 2 by reaction of (35) with an appropriate organometallic species to give (36) via a 1,4-conjugate addition reaction. Indanone (36) is then converted to the final compound (37) by the procedures previously described in Scheme V.

SCHEME IX

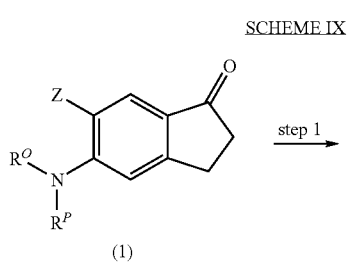

(1)

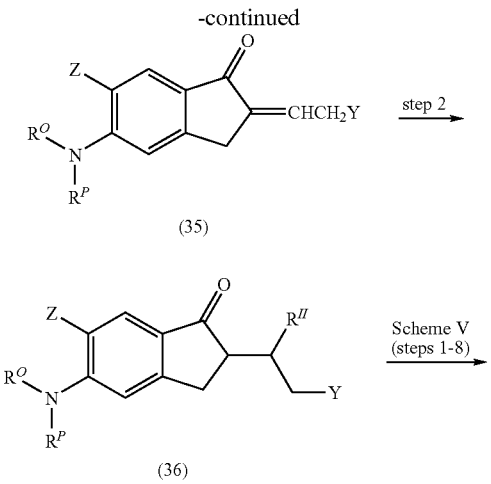

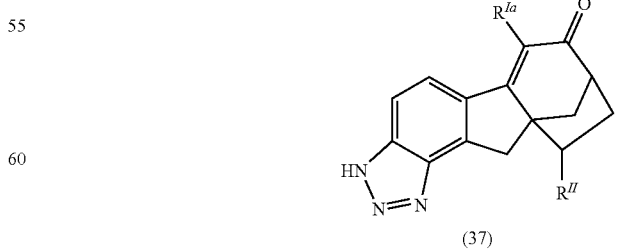

(37)

Representative reagents and reaction conditions indicated in Scheme IX as steps 1-2 are as follows:

| Step 1 | BnOCH$_2$CHO, KOH, MeOH or | Y = OBn |
| --- | --- | --- |
| | i) LiN(TMS)$_2$, THF, −78° C. to rt | |
| | ii) BnOCH$_2$CHO | |
| | iii) MsCl, Et$_3$N, CH$_2$Cl$_2$ | |
| Step 2 | R$^{II}$MgBr, CuBr•SMe$_2$, THF −78° C. to rt or | |
| | R$^{II}_2$CuLi, THF −78° C. to rt | |

Final compounds bearing substituents at the 10-position are prepared by the methods summarized in Scheme X. Intermediate (38), where R$^Q$ represents hydrogen or a nitrogen protecting group, is oxidized by N-halosuccinimide reagents and the like (step 1) to afford the 10-halo products (39). A final deprotection, if needed, then provides the final compounds (40). The 10-halo compounds (39) undergo displacement reactions with suitable nucleophilic reagents (step 2) to afford additional products (41). A final deprotection, if needed, then provides the final compounds (42). If desired, this methodology can be extended to the preparation of 10,10-disubstituted products. The 10-oxo product (43) is available by potassium persulfate oxidation of (38). Reduction of (43) gives 10-hydroxy compounds (41, R$^{IIIb}$=OH). A final deprotection of (43), if needed, provides the final compounds (44).

Representative reagents and reaction conditions indicated in Scheme X as steps 1-4 are as follows:

| Step 1 | NCS, AIBN, CCl$_4$, rt to 80° C. | R$^{IIIa}$ = Cl |
| --- | --- | --- |
| | NBS, AIBN, CCl$_4$, rt to 80° C. | R$^{IIIa}$ = Br |
| Step 2 | pyridine-HF, TFA, rt to 50° C. | R$^{IIIb}$ = F |
| | AgOAc, DMF, rt to 100° C. | R$^{IIIb}$ = OAc |
| | i) AgOAc, DMF, rt to 100° C. | R$^{IIIb}$ = OH |
| | ii) NaOH, H$_2$O, MeOH | |
| Step 3 | K$_2$S$_2$O$_8$, H$_2$O, MeCN, rt to 80° C. | |
| Step 4 | NaBH$_4$, MeOH, 0° C. to rt | R$^{IIIb}$ = OH |

Modifications of the C-6 ketone of (38) are outlined in Scheme XI. In step 1, the ketone is reacted with a hydroxylamine, alkoxylamine or hydrazine reagent to give the 6-imino products (45). Ketone (9) also reacts with ylide reagents (step 2) to afford 6-alkylidene derivatives (47). Deprotection, if needed, provides the final products (46) and (48).

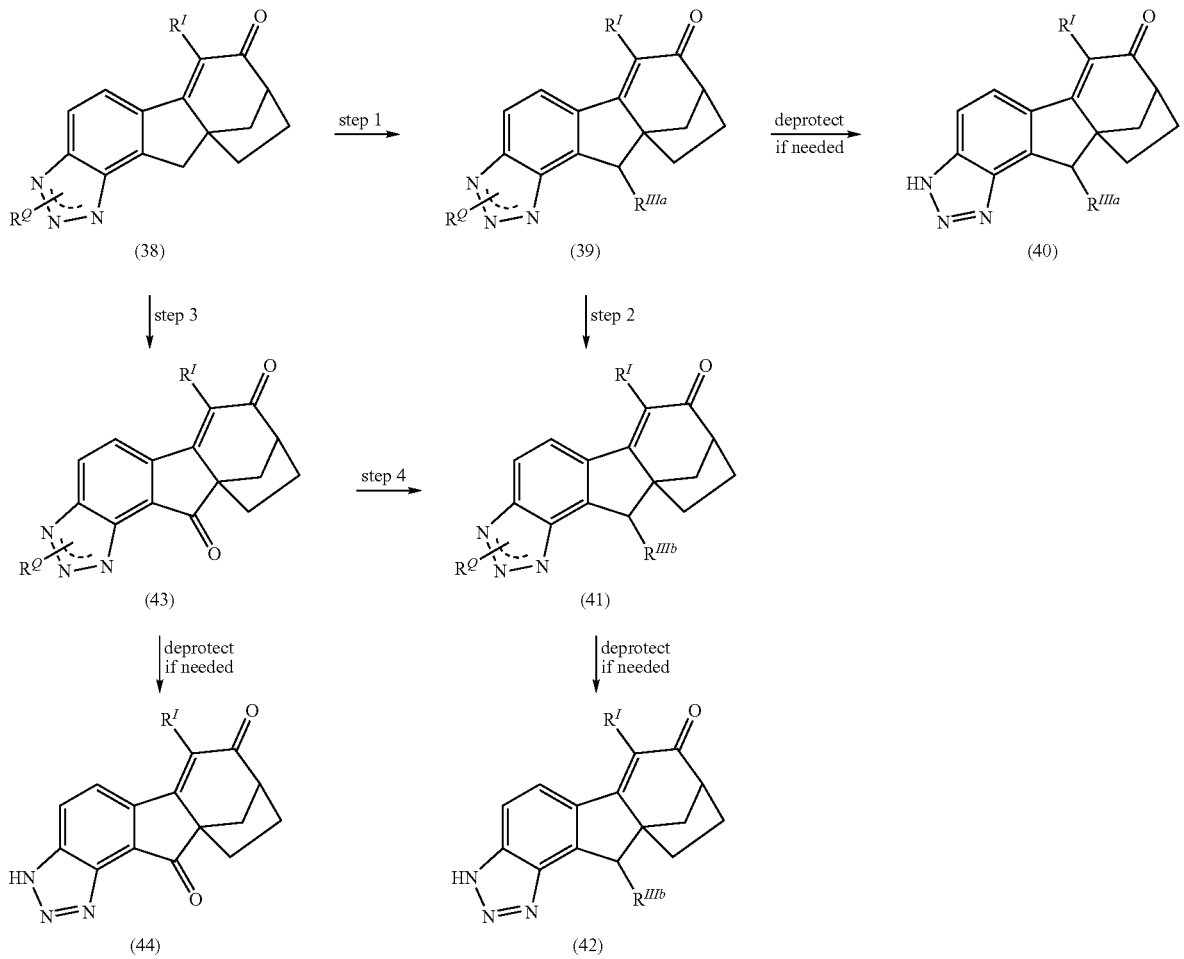

SCHEME X

SCHEME XI

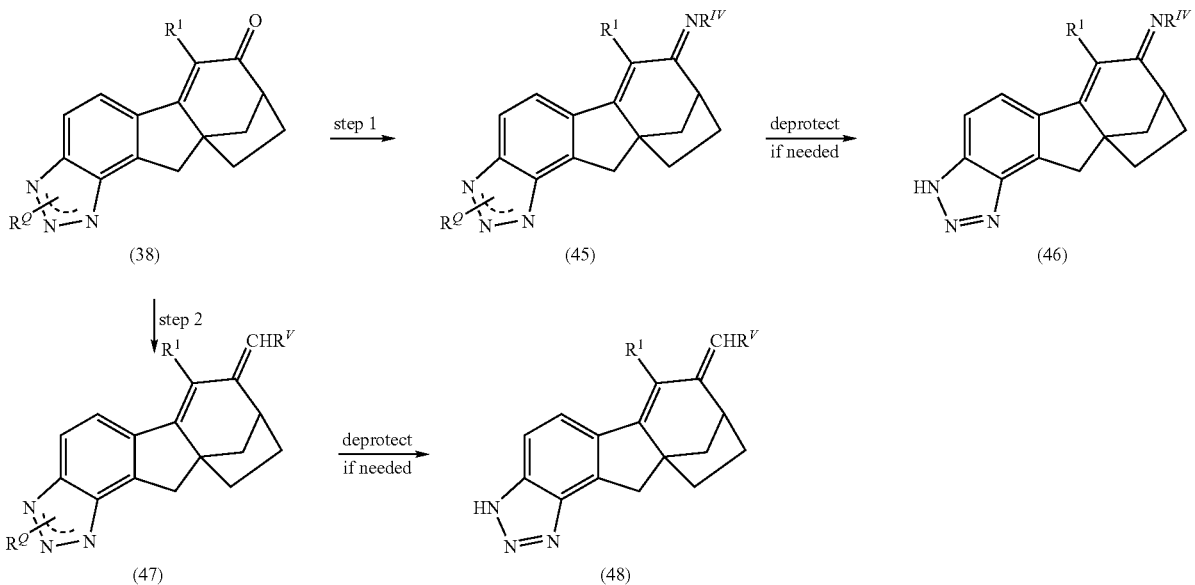

Representative reagents and reaction conditions indicated in Scheme XI as steps 1-2 are as follows:

| Step 1 | NH$_2$OR$^a$·HCl, pyridine, rt to 60° C. | R$^{IV}$ = OR$^a$ |
|---|---|---|
|  | NH$_2$NR$^a$R$^a$, EtOH, rt | R$^{IV}$ = NR$^a$R$^a$ |
| Step 2 | Ph$_3$P$^+$CH$_2$R$^{VI}$Br$^-$, BuLi, THF, 0 to 50° C. | |

In Schemes I-XI, the various R groups often contain protected functional groups which are deblocked by conventional methods. The deblocking procedure can occur at the last step or at an intermediate stage in the synthetic sequence. Many well known protection-deprotection schemes can be used to prevent unwanted reactions of functional groups contained in the various R substituents.

The final compounds prepared according to Schemes I-XI have chiral centers and can be resolved into the separate enantiomers by known methods, for example by chiral HPLC. Separation into the individual enantiomers can also be accomplished at a number of intermediate stages in the synthesis.

The following specific examples, while not limiting, serve to illustrate the methods of preparation of the compounds of the present invention.

EXAMPLE 1

Synthesis of (8R,10aS)-6-(triflouromethl)-3,9,10,11-tetrahydro-8,10a-methanocylohepta[1,2]indeno[4,5-d][1,2,3]triazol-7(8H)-One

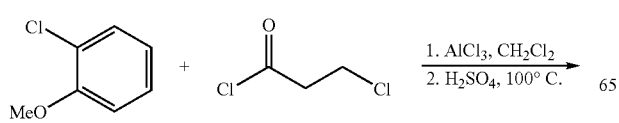

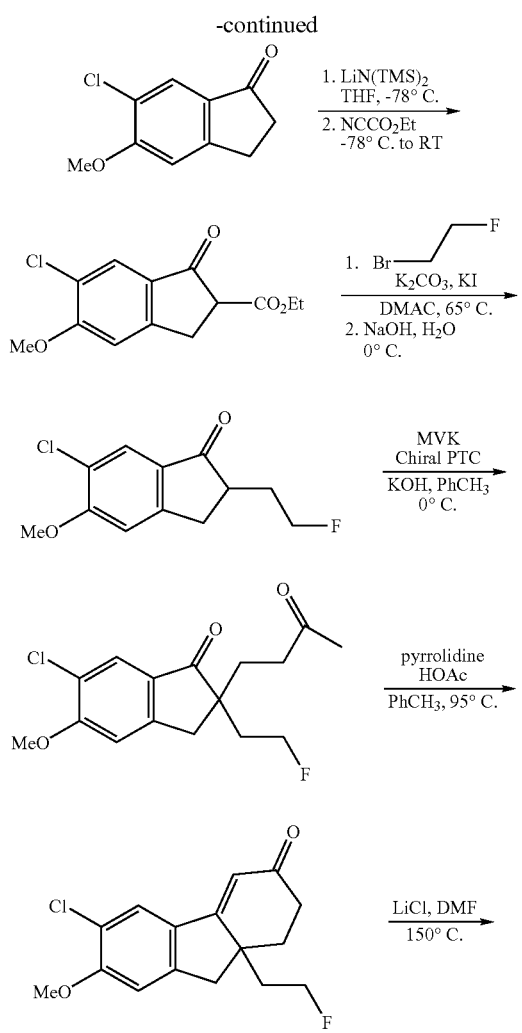

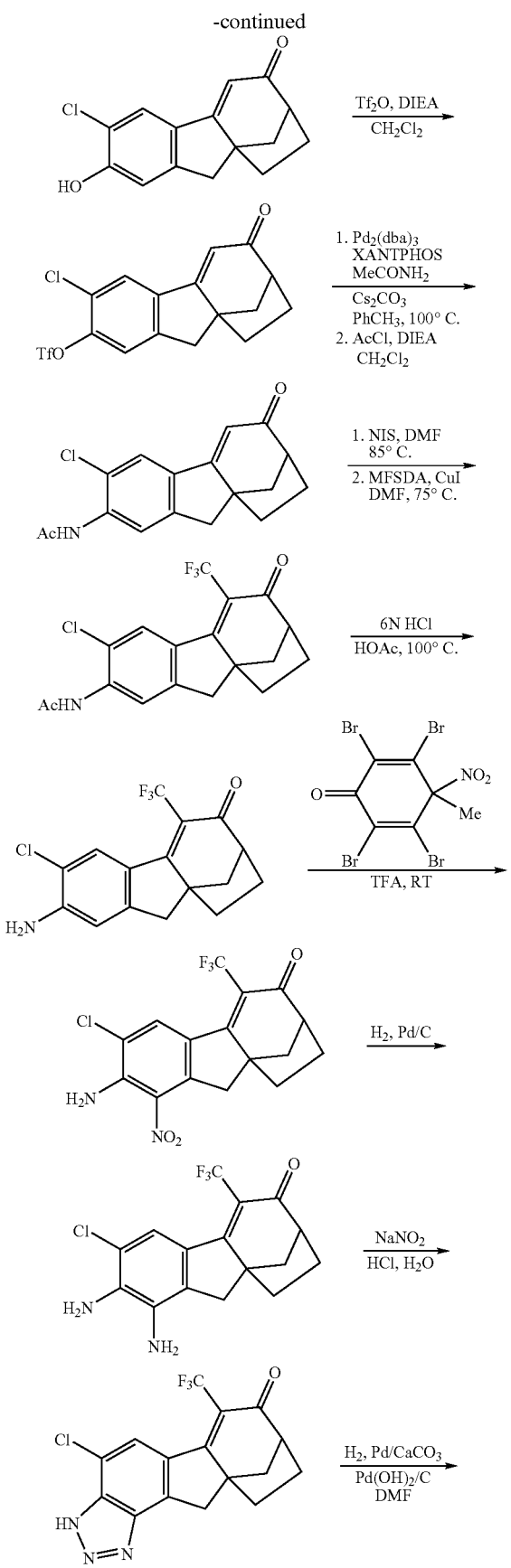

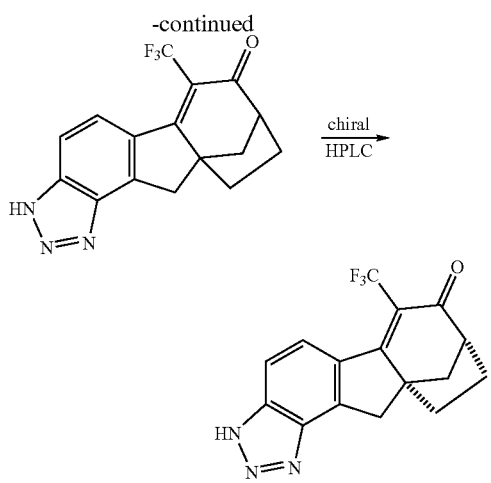

Step 1: 6-chloro-5-methoxyindan-1-one

To a solution of 1-chloro-2-methoxybenzene (12.8 mL, 100 mmol) and 3-chloropropanoyl chloride (10.5 mL, 110 mmol) in $CH_2Cl_2$ (100 mL) at 0° C. was added $AlCl_3$ (14.6 g, 110 mmol) portionwise during about 1 minute. After 30 minutes, sulfuric acid (300 mL) was poured slowly into the reaction mixture during about 3 minutes. The $CH_2Cl_2$ was removed by rotary evaporation under reduced pressure and the viscous residue was stirred at 100 ° C. for 2 hours. After cooling to ~50° C., the viscous reaction mixture was poured cautiously onto 1.5 L of ice and allowed to stand overnight. The mixture was filtered and the cake of crude product was washed with water. The crude product was dissolved in 500 mL of 2% MeOH in $CH_2Cl_2$, dried over a mixture of $Na_2CO_3$ (~10 g) and $Na_2SO_4$ (~20 g), filtered and concentrated under vacuum to give 6-chloro-5-methoxyindan-1-one as an off-white solid.

Step 2: ethyl 6-chloro-5-methoxy-1-oxoindane-2-carboxylate

To a solution of 6-chloro-5-methoxyindan-1-one (27.6 g, 141 mmol) in THF (630 mL) at −78° C. was added a 1.0M solution of lithium bis(trimethylsilyl)amide in THF (309 mL, 309 mmol) and then the solution was slowly warmed to ca −50° C. during 1 hour. After re-cooling to −78° C., ethyl cyanoformate (21.3 mL, 216 mmol) was introduced and the reaction mixture was allowed to warm to room temperature during 2 hours. After quenching with 300 mL of 1N HCl, most of the THF was removed by rotary evaporation under reduced pressure. The residual mixture was extracted with EtOAc and the organic layer was washed with dilute aqueous $NaHCO_3$ and dried over $Na_2SO_4$. Filtration through a pad of silica and removal of the solvent under reduced pressure gave ethyl 6-chloro-5-methoxy-1-oxoindane-2-carboxylate as a brown oil.

Step 3: 6-chloro-2-(2-fluoroethyl)-5-methoxyindan-1-one

To a solution of ethyl 6-chloro-5-methoxy-1-oxoindane-2-carboxylate (crude product from the preceding step, ~141 mmol) in anhydrous dimethylacetamide (540 mL) was added $K_2CO_3$ (39 g, 282 mmol), KI (46.8 g, 282 mmol) and 1-bromo-2-fluoroethane (13.5 mL, 183 mmol) and the mixture was stirred and heated at 65° C. for 6 hours. The reaction mixture was diluted with TUF (540 mL) and water (540 mL) and then cooled to 0° C. and treated with 5N aqueous NaOH (84 mL, 423 mmol). After 2 hours at 0° C., the reaction was quenched with 1N aqueous HCl (~450 mL). Most of the THF was removed by rotary evaporation under reduced pressure and the aqueous residue was extracted with EtOAc. The organic layer was washed with saturated NaHCO$_3$, dried over MgSO$_4$, filtered through a pad of silica gel and concentrated to give 6-chloro-2-(2-fluoroethyl)-5-methoxyindan-1-one.

Step 4: 6-chloro-2-(2-fluoroethyl)-5-methoxy-2-(3-oxobutyl)indan-1-one

To a solution of 6-chloro-2-(2-fluoroethyl)-5-methoxyindan-1-one (34 g, 140 mmol) in toluene (1500 mL) was added N-[4-(trifluoromethyl)benzyl]cinchoninium bromide (13 g, 24 mmol) and the mixture was stirred at room temperature for 30 minutes. After cooling to 0° C., methyl vinyl ketone (20 mL, 240 mmol) was added followed by potassium hydroxide pellets (85%, 34 g, ~52 mmol) and the mixture was vigorously stirred for 90 minutes. The reaction mixture was diluted with dichloromethane (1000 mL), dried with MgSO$_4$ and filtered. The filtrate was filtered through a pad of silica gel, washing with Et$_2$O and EtOAc. The filtrate was concentrated under reduced pressure and the residue was chromatographed on silica gel (elution with 30% to 50% EtOAc/hexanes) to give 6-chloro-2-(2-fluoroethyl)-5-methoxy-2-(3-oxobutyl) indan-1-one as a yellow oil. Analysis by chiral HPLC indicated an enantiomeric ratio of approximately 2:1 favoring the desired (2S)-enantiomer. This enantiomerically enriched material was utilized for the remainder of the synthesis.

Step 5: 6-chloro-9a-(2-fluoroethyl)-7-methoxy-1,2,9,9a-tetrahydro-3H-fluoren-3-one To a solution of 6-chloro-2-(2-fluoroethyl)-5-methoxy-2-(3-oxobutyl)indan-1-one (32 g, 102 mmol) in toluene (1000 mL) were added acetic acid (7.0 mL, 120 mmol) and pyrrolidine (10 mL, 120 mmol) and the solution was heated at 95° C. for 2 hours. After cooling to room temperature, the reaction mixture was diluted with EtOAc (1000 mL), washed with water and saturated aqueous NaHCO$_3$, and dried over MgSO$_4$. Filtration through a pad of silica gel and removal of the solvent under vacuum gave 6-chloro-9a-(2-fluoroethyl)-7-methoxy-1,2,9,9a-tetrahydro-3H-fluoren-3-one as a solid.

Step 6: 3-chloro-2-hydroxygibba-1,3,4a(10a),4b-tetraen-6-one

To a mixture of 6-chloro-9a-(2-fluoroethyl)-7-methoxy-1,2,9,9a-tetrahydro-3H-fluoren-3-one (18.5 g, 63 mmol) and lithium chloride (26.5 g, 630 mmol) was added DMF (250 mL) and the mixture was stirred and heated at 150° C. for 2 days. After cooling to room temperature, the reaction mixture was partitioned between EtOAc and water. The organic phase was washed with water (2×) and brine and dried over MgSO$_4$. Removal of the solvent under vacuum gave a solid which was partially dissolved in 5% MeOH/CH$_2$Cl$_2$ (300 mL) and the resulting suspension was filtered to give 3-chloro-2-hydroxygibba-1,3,4a(10a),4b-tetraen-6-one as a brown solid. The filtrate was concentrated under vacuum and the residue was partially dissolved in 200 mL of CH$_2$Cl$_2$ and filtered to give a second crop of 3-chloro-2-hydroxygibba-1,3,4a(10a),4b-tetraen-6-one. The filtrate was concentrated under vacuum and the residue was flash chromatographed on silica gel (elution with 10 to 100% EtOAc/hexanes) to give additional 3-chloro-2-hydroxygibba-1,3,4a(10a),4b-tetraen-6-one.

Step 7: 3-chloro-6-oxogibba-1,3,4a(10a),4b-tetraen-2-yl trifluoromethanesulfonate To a suspension of 3-chloro-2-hydroxygibba-1,3,4a(10a), 4b-tetraen-6-one (5.71 g, 21.2 mmol) in dichloromethane (80 mL) was added N,N-diisopropylethylamine (4.0 mL, 23.2 mmol). The resulting brown solution was cooled to 0° C. and trifluoromethanesulfonic anhydride (3.9 mL, 23.2 mmol) was added. After 35 minutes, the reaction mixture was directly loaded onto a silica gel column and chromatographed (elution with 10 to 100% EtOAc/hexanes) to give the product as a brown oil. The oil was dissolved in dichloromethane and dried over MgSO$_4$. Evaporation under vacuum gave a solid which was dissolved in toluene and then evaporated under vacuum to give 3-chloro-6-oxogibba-1,3,4a(10a),4b-tetraen-2-yl trifluoromethanesulfonate as a brown solid.

Step 8: N-[3-chloro-6-oxogibba-1,3,4a(10a),4b-tetraen-2-yl] acetamide

To a mixture of 3-chloro-6-oxogibba-1,3,4a(10a),4b-tetraen-2-yl trifluoromethanesulfonate (6.04 g, 15.4 mmol), cesium carbonate (11.01 g, 33.9 mmol), 4,5-bis(diphenylphosphino)-9,9-dimethylxanthene (xantphos, 1.33 g, 2.31 mmol), tris(dibenzylideneacetone)dipalladium(0) [Pd$_2$(dba)$_3$, 0.704 g, 0.77 mmol] and acetamide (2.00 g, 33.9 mmol) was added toluene (77 mL). The reaction flask was capped and the stirred reaction mixture was heated at 100° C. under nitrogen. After heating for 16 hours, additional xantphos (0.233 g, 0.403 mmol), Pd$_2$(dba)$_3$ (0.140 g, 0.153 mmol) and acetamide (1.00 g, 16.9 mmol) were added. After heating for an additional 24 hours, the reaction mixture was cooled to room temperature, diluted with 5% MeOH/ CH$_2$Cl$_2$, and filtered through a pad of silica gel. Evaporation under reduced pressure gave an oily brown solid. The solid was dissolved in dichloromethane (60 mL) and N,N-diisopropylethylamine (2.8 mL, 16 mmol) was added followed by acetyl chloride (1.4 mL, 19 mmol). After 10 minutes, the solution was loaded directly onto a silica gel column and chromatographed (elution with 10 to 100% EtOAc/hexanes) to give N-[3-chloro-6-oxogibba-1,3,4a(10a),4b-tetraen-2-yl]acetamide as an orange solid.

Step 9: N-[3-chloro-6-oxo-5-(trifluoromethyl)gibba-1,3,4a (10a),4b-tetraen-2-yl]acetamide To a solution of N-[3-chloro-6-oxogibba-1,3,4a(10a),4b-tetraen-2-yl]acetamide (3.85 g, 12.8 mmol) in DMF at 85° C. was added N-iodosuccinimide (4.00 g, 17.7 mmol). After heating for 18 hours, the reaction mixture was cooled to room temperature and diluted with DMF (160 mL). Copper(I) iodide (3.65 g, 19.2 mmol), methyl(fluorosulfonyl)difluoroacetate (11.5 mL, 90 mmol) and N,N-diisopropylethylamine (15.8 mL, 90 mmol) were added and the mixture was heated to 75° C. After 140 minutes, the reaction mixture was cooled to room temperature and filtered through a pad of silica gel, washing with EtOAc. The filtrate was partitioned between EtOAc and water and the organic layer was washed with 5% aqueous NaHCO$_3$, water and brine. Drying over MgSO$_4$ and evaporation under vacuum gave an oil which was chromatographed on silica gel (elution with 10 to 85% EtOAc/hexanes) to give N-[3-chloro-6-oxo-5-(trifluoromethyl)gibba-1,3,4a (10a),4b-tetraen-2-yl]acetamide as an orange foam.

Step 10: 2-amino-3-chloro-5-(trifluoromethyl)gibba-1,3,4a (10a),4b-tetraen-6-one To a solution of N-[3-chloro-6-oxo-5-(trifluoromethyl) gibba-1,3,4a(10a),4b-tetraen-2-yl]acetamide (3.80 g, 10.3 mmol) in 40 mL of acetic acid was added 6N hydrochloric acid (40 mL) and the solution was heated at 80° C. After 85 minutes, the reaction mixture was cooled to room temperature and partitioned between EtOAc and 5% aqueous NaHCO$_3$. Some orange precipitate formed which was thoroughly extracted with EtOAc. The combined organic solutions were washed with water and brine and dried over MgSO$_4$. Removal of the solvent under reduced pressure gave 2-amino-3-chloro-5-(trifluoromethyl)gibba-1,3,4a(10a),4b-tetraen-6-one as an orange solid.

Step 11: 2-amino-3-chloro-1-nitro-5-(trifluoromethyl)gibba-1,3,4a(10a),4b-tetraen-6-one To a solution of 2-amino-3-chloro-5-(trifluoromethyl) gibba-1,3,4a(10a),4b-tetraen-6-one (2.9 g, 8.9 mmol) in trifluoroacetic acid (19 mL) was added 2,3,5,6-tetrabromo-4-methyl-4-nitrocyclohexa-2,5-dienone and the thick suspension was stirred at room temperature. After 70 minutes, the mixture was cooled to 0° C. and filtered, washing with cold trifluoroacetic acid. The filtrate was concentrated under vacuum and the residue was partitioned between EtOAc/CH$_2$Cl$_2$ (10:1) and 10% aqueous K$_2$CO$_3$. The organic phase was washed thoroughly with 10% aqueous K$_2$CO$_3$ followed by 5% aqueous NaHCO$_3$ and then brine. After drying over MgSO$_4$, evaporation of the solvent under vacuum gave 2-amino-3-chloro-1-nitro-5-(trifluoromethyl)gibba-1,3,4a(10a),4b-tetraen-6-one as a tan solid.

Step 12: 1,2-diamino-3-chloro-5-(trifluoromethyl)gibba-1,3,4a(10a),4b-tetraen-6-one To a suspension of 2-amino-3-chloro-1-nitro-5-(trifluoromethyl)gibba-1,3,4a(10a),4b-tetraen-6-one(3.3 g, 8.9 mmol) in 1:1 MeOH/EtOAc (270 mL) was added potassium acetate (1.86 g, 19 mmol). The mixture was gently warmed to give a brown solution which was hydrogenated at atmospheric pressure over 10% palladium on carbon (1.25 g). After 35 minutes, the mixture was filtered through NaHCO$_3$ on top of a pad of silica gel, washing with 5% MeOH/CH$_2$Cl$_2$. The filtrate was concentrated under reduced pressure and the residue was chromatographed on silica gel (elution with 25% to 100% EtOAc in hexanes) to give 1,2-diamino-3-chloro-5-(trifluoromethyl)gibba-1,3,4a(10a),4b-tetraen-6-one as an orange solid.

Step 13: 4-chloro-6-(trifluoromethyl)-3,9,10,11-tetrahydro-8,10a-methanocyclohepta-[1,2]indeno[4,5-d][1,2,3]triazol-7(8H)-one To a suspension of 1,2-diamino-3-chloro-5-(trifluoromethyl)gibba-1,3,4a(10a),4b-tetraen-6-one (2.1 g, 6.1 mmol) in ethanol (120 mL) were added water (2 mL) and 12N hydrochloric acid (6.2 mL). The resulting orange solution was cooled to 0° C. and 3M aqueous sodium nitrite (6.2 mL, 18.6 mmol) was added. After 40 minutes, the solution was partitioned between EtOAc and water. The organic layer was washed with brine, dried over MgSO$_4$ and evaporated under vacuum to give 4-chloro-6-(trifluoromethyl)-3,9,10,11-tetrahydro-8,10a-methanocyclohepta-[1,2]indeno[4,5-d][1,2,3]triazol-7(8H)-one as an orange solid.

Step 14: 6-(trifluoromethyl)-3,9,10,11-tetrahydro-8,10a-methanocyclohepta-[1,2]indeno[4,5-d][1,2,3]triazol-7(8H)-one To a solution of 4-chloro-6-(trifluoromethyl)-3,9,10,11-tetrahydro-8,10a-methanocyclohepta-[1,2]indeno[4,5-d][1,2,3]triazol-7(8H)-one (2.3 g, crude product from the preceding step, ~6.1 mmol) in DMF (230 mL) were added 20% Pd(OH)$_2$ on carbon (1 g) and 5% palladium on calcium carbonate (1 g) and the mixture was hydrogenated at atmospheric pressure. After 29 hours, additional 20% Pd(OH)$_2$ on carbon (175 mg) and 5% palladium on calcium carbonate (175 mg) were added. After 24 hours more, the mixture was filtered through a pad of Celite®, washing thoroughly with EtOAc. The filtrate was partitioned between EtOAc and water which had been acidified with a small amount of 1N hydrochloric acid. The aqueous layer was thoroughly extracted with EtOAc and the combined organic layers were washed with 1N hydrochloric acid, water and brine. After drying over MgSO$_4$, the solvent was removed under reduced pressure to give an oily solid which was dissolved in dichloromethane and evaporated to give a solid. Chromatography on silica gel (elution with 1:1 EtOAc/hexanes+0.1% HOAc followed by 99:99:2 EtOAc/hexanes/methanol+0.1% HOAc) gave 6-(trifluoromethyl)-3,9,10,11-tetrahydro-8,10a-methanocyclohepta-[1,2]indeno[4,5-d][1,2,3]triazol-7(8H)-one as a pale yellow solid.

Step 15: (8R,10aS)-6-(trifluoromethyl)-3,9,10,11-tetrahydro-8,10a-methanocyclohepta-[1,2]indeno[4,5-d][1,2,3]triazol-7(8H)-one 6-(trifluoromethyl)-3,9,10,11-tetrahydro-8,10a-methanocyclohepta-[1,2]indeno[4,5-d][1,2,3]triazol-7(8H)-one [1.8 g, (8R,10aS): (8S,10aR) enantiomeric ratio ~2:1] was dissolved in 1/1 ethanol/methanol (130 mL) and resolved by chiral HPLC on a 2.0×25 cm Daicel Chiralcel OJ column (4 mL injections, elution with 35% EtOH:Heptane at 7.5 mL/min, fractions monitored at 310 nm). The pure fractions containing the first enantiomer to elute (enantiomer A) were combined and concentrated to give (8R,10aS)-6-(trifluoromethyl)-3,9,10,11-tetrahydro-8,10a-methanocyclohepta[1,2]indeno[4,5-d][1,2,3]triazol-7(8H)-one as a white solid which had a negative rotation. The fractions containing the second enantiomer to elute (enantiomer B) were combined and concentrated to give(8S,10aR)-6-(trifluoromethyl)-3,9,10,11-tetrahydro-8,10a-methanocyclohepta[1,2]indeno[4,5-d][1,2,3]triazol-7(8H)- one as a solid which had a positive rotation.

Enantiomer A: $[\alpha]_D = -263°$ (MeOH).

$^1$H NMR (CD$_3$CN, 600 MHz): δ 1.61 (dddd, 1H), 1.74-1.79 (m, 1H), 1.95-2.05 (m, 1H), 2.05 (dd, 1H), 2.12 (brd, 1H), 2.32-2.38 (m, 1H), 3.02 (dd, 1H), 3.55 (d, 1H), 3.68 (d, 1H), 7.77 (d, 1H), 7.87 (dq, 1H).

Mass spectrum: (ESI) m/z=320 (M+H).

EXAMPLES 2-7

The following compounds were prepared using methods analogous to those described in the preceding examples:

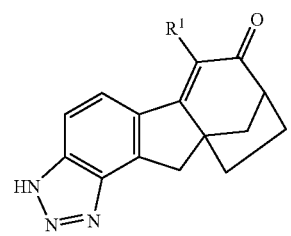

| | | |
|---|---|---|
| 2 | R$^1$ = Br | 6-bromo-3,9,10,11-tetrahydro-8,10a-methanocyclohepta[1,2]indeno[4,5-d][1,2,3]triazol-7(8H)-one |

$^1$H NMR (CDCl$_3$, 500 MHz): δ 1.79-1.85(m, 1H), 1.97-2.28(m, 4H), 2.39-2.46(m, 1H), 3.42(dd, 1H), 3.67-3.76(m, 2H), 7.78-7.82(m, 1H), 8.81(d, 1H).

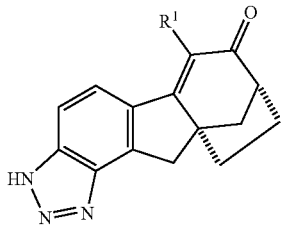

| 3 | R¹ = Cl | (8R,10aS)-6-chloro-3,9,10,11-tetrahydro-8,10a-methanocyclohepta[1,2]indeno[4,5-d][1,2,3]triazol-7(8H)-one |

¹H NMR (d⁶-DMSO, 600 MHz): δ 1.54-1.62(m, 1H), 1.76-1.84(m, 1H), 2.03-2.11(m, 2H), 2.13(d, 1H), 2.28-2.37(m, 1H), 3.15(dd, 1H), 3.53(d, 1H), 3.65(d, 1H), 7.92(d, 1H), 8.35(d, 1H).

| 4 | R¹ = Ph | (8R,10aS)-6-phenyl-3,9,10,11-tetrahydro-8,10a-methanocyclohepta[1,2]indeno[4,5-d][1,2,3]triazol-7(8H)-one |

¹H NMR (CDCl₃, 500 MHz): δ 1.9-2.0(m, 1H), 2.0-2.2(m, 2H), 2.20(dd, 1H), 2.31(d, 1H), 2.4-2.5(m, 1H), 3.29(dd, 1H), 3.6-3.8(m, 2H), 6.61(d, 1H), 7.0-7.6(m, 6H).

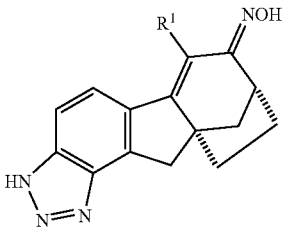

| 5 | R¹ = Cl | (8R,10aS)-6-chloro-3,9,10,11-tetrahydro-8,10a-methanocyclohepta[1,2]indeno[4,5-d][1,2,3]triazol-7(8H)-one oxime |

¹H NMR (CD₃CN, 600 MHz): δ 1.55-1.61(m, 1H), 1.83(d, 1H), 1.86-1.93 (m, 2H), 1.99(dd, 1H), 2.22-2.30(m, 1H), 3.45(d, 1H), 3.57(d, 1H), 4.09(dd, 1H), 7.79(d, 1H), 8.39(d, 1H).

| 6 | R¹ = CF₃ | (8R,10aS)-6-(trifluoroinethyl)-3,9,10,11-tetrahydro-8,10a-methanocyclohepta[1,2]indeno-[4,5-d][1,2,3]triazol-7(8H)-one oxime |

¹H NMR (CD₃CN, 600 MHz): δ 1.53-1.59(m, 1H), 1.70-1.75(m, 1H), 1.73(d, 1H), 1.83(ddd, 1H), 1.95(dd, 1H), 2.18-2.25(m, 1H), 3.43(d, 1H), 3.61(d, 1H), 4.00(dd, 1H), 7.72(d, 1H), 7.78(dd, 1H).

| 7 | R¹ = Ph | (8R,10aS)-6-phenyl-3,9,10,11-tetrahydro-8,10a-methanocyclohepta[1,2]indeno[4,5-d][1,2,3]triazol-7(8H)-one oxime |

¹H NMR (d⁶-DMSO, 600 MHz): δ 1.61-1.65(m, 1H), 1.80-1.95(m, 2H), 1.95-2.00(m, 1H), 3.2-3.6(m, 2H), 3.97(bs, 1H), 3.6-3.8(m, 2H), 7.0-7.6(m, 7H).

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ER-α or ER-β extracts are diluted 1:400 in phosphate buffered saline containing 6 mM α-monothiolglycerol. 200 μL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, and 6 mM α-monothiolglycerol. To set up the assay in these receptor coated plates, add 178 ul of the same buffer to each well of the 96 well plate. Then add 20 ul of a 10 nM solution of ³H-estradiol to each well of the plate.

Test compounds are evaluated over a range of concentrations from 0.01 nM to 1000 nM. The test compound stock solutions should be made in 100% DMSO at 100× the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

The compounds of Examples 1-7 exhibit binding affinities to the estrogen receptor α-subtype in the range of $IC_{50}=13$ to >10,000 nm, and to the estrogen receptor β-subtype in the range of $IC_{50}=3$ to 146 nm.

Pharmaceutical Composition

As a specific embodiment of this invention, 25 mg of compound of Example 1, is formulated with sufficient finely divided lactose to provide a total amount of 580 to 590 mg to fill a size 0, hard-gelatin capsule.

What is claimed is:

1. A compound of the formula:

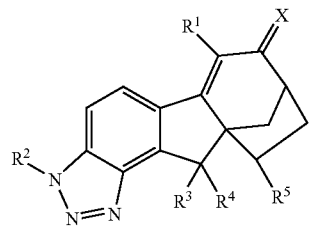

wherein X is O— or N—OH;

R¹ is hydrogen, fluoro, chloro, bromo, iodo, or $C_{1-4}$alkyl, wherein said alkyl group is optionally substituted with 1, 2 or 3 groups selected from the group consisting of fluoro, chloro, and bromo;

R² is hydrogen;

R³ is hydrogen;

R⁴ is hydrogen;

R⁵ is hydrogen;

or a pharmaceutically acceptable salt; or a stereoisomer thereof.

2. The compound of claim 1 which is 6-(trifluoromethyl)-3,9,10,11-tetrahydro-8,10a-methanocyclohepta[1,2]indeno [4,5-d][1,2,3]triazol-7(8H)-one;

6-chloro-3,9,10,11-tetrahydro-8,10a-methanocyclohepta [1,2]indeno[4,5-d][1,2,3]triazol-7(8H)-one;

6-bromo-3,9,10,11-tetrahydro-8,10a-methanocyclohepta [1,2]indeno[4,5-d][1,2,3]triazol-7(8H)-one; 6-chloro-3, 9,10,11-tetrahydro-8,10a-methanocyclohepta[1,2]indeno[4,5-d][1,2,3]triazol-7(8H)-one oxime; and 6-(trifluoromethyl)-3,9,10,11-tetrahydro-8,10a-methanocyclohepta[1,2]indeno[4,5-d][1,2,3]triazol-7(8H)-one oxime;

or a pharmaceutically acceptable salt; or a stereoisomer thereof.

3. The compound of claim 2 which is
(8R,10aS)-6-(trifluoromethyl)-3,9,10,11-tetrahydro-8, 10a-methanocyclohepta[1,2]indeno[4,5-d][,1,2,3]triazol-7(8H)-one;
(8R,10aS)-6-chloro-3,9,10,11-tetrahydro-8,10a-methanocyclohepta[1,2]indeno[4,5-d][1,2,3]triazol-7(8H)-one;
(8R,10aS)-6-bromo-3,9,10,11-tetrahydro-8,10a-methanocyclohepta[1,2]indeno [4,5-d][1,2,3 ]triazol-7(8H)-one;
(8R,10aS)-6-chloro-3,9,10,11-tetrahydro-8,10a-methanocyclohepta[1,2]indeno[4,5-d][1 ,2,3]triazol-7(8H)-one oxime; and
(8R,10aS)-6-(trifluoromethyl)-3,9,10,11-tetrahydro-8, 10a-methanocyclohepta[1,2]indeno[4,5-d][1,2,3]triazol-7(8H)-one oxime;
or a pharmaceutically acceptable salt thereof.

4. A compound which is (8R,10aS)-6-(trifluoromethyl)-3, 9,10,11-tetrahydro-8,10a-methanocyclohepta[1,2]indeno[4, 5-d][1,2,3]triazol-7(8H)-one.

5. A pharmaceutical composition comprising a compound of claim 1 and a pharmaceutically acceptable carrier.

6. A pharmaceutical composition comprising a compound of claim 1 and another agent selected from the group consisting of an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; an aromatase inhibitor; or a pharmaceutically acceptable salt or mixture thereof, and a pharmaceutically acceptable carrier.

7. A method for treating uterine fibroid disease, hot flashes, perimenopausal depression, or premenstrual syndrome in a mammal in need thereof, which comprises administering to said mammal a therapeutically effective amount of a compound of claim 1.

8. A method for treating uterine fibroid disease, hot flashes, perimenopausal depression, or premenstrual syndrome in mammal in need thereof, which comprises administering to said mammal a therapeutically effective amount of a composition of claim 6.

9. A compound selected from 6-phenyl-3,9,10,11-tetrahydro-8,10a-methanocyclohepta[1,2]indeno [4,5-d][1,2,3]triazol-7(8H)-one, and 6-phenyl-3,9,10,11-tetrahydro-8,10a-methanocyclohepta[1,2]indeno[4,5-d][1,2,3]triazol-7(8H)-one oxime; or a pharmaceutically acceptable salt or a stereoisomer thereof.

10. The compound of claim 9 selected from (8R,10aS)-6-phenyl-3,9,10,11-tetrahydro-8,10a-methanocyclohepta[1,2]indeno[4,5-d][1,2,3]triazol-7(8H)-one, and (8R, 10aS)-6-phenyl-3,9,10,11-tetrahydro-8,10a-methanocyclohepta[1,2]indeno [4,5-d][1,2,3]triazol-7(8H)-one oxime; or a pharmaceutically acceptable salt thereof.

11. The compound of claim 3, which is (8R,10aS)-6-(trifluoromethyl)-3,9,10,11-tetrahydro-8,10a-methanocyclohepta[1,2]indeno[4,5-d][1,2,3]triazol-7(8H)-one; or a pharmaceutically acceptable salt thereof.

12. The compound of claim 2, which is 6-(trifluoromethyl)-3,9,10,11-tetrahydro-8,10a-methanocyclohepta[1,2]indeno[4,5-d][1,2,3]triazol-7(8H)-one or a pharmaceutically acceptable salt thereof; or a stereoisomer thereof.

13. The compound of claim 2, which is 6-(trifluoromethyl)-3,9,10,11-tetrahydro-8,10a-methanocyclohepta[1,2]indeno[4,5-d][1,2,3]triazol-7(8H)-one.

14. A pharmaceutical composition comprising the compound of claim 7 and a pharmaceutically acceptable carrier.

15. A pharmaceutical composition comprising the compound of claim 13 and a pharmaceutically acceptable carrier.

16. A method for treating uterine fibroid disease, hot flashes, perimenopausal depression, or premenstrual syndrome in a mammal in need thereof, which comprises administering to said mammal a therapeutically effective amount of the compound of claim 4.

17. A method for treating uterine fibroid disease, hot flashes, perimenopausal depression, or premenstrual syndrome in a mammal in need thereof, which comprises administering to said mammal a therapeutically effective amount of the compound of claim 13.

* * * * *